(12) United States Patent
Hackam et al.

(10) Patent No.: US 11,413,299 B2
(45) Date of Patent: Aug. 16, 2022

(54) COMPOSITIONS AND METHODS FOR TREATMENT OF INFLAMMATORY DISORDERS

(71) Applicants: THE JOHNS HOPKINS UNIVERSITY, Baltimore, MD (US); University of Pittsburgh—Of the Commonwealth System of Higher Education, Pittsburgh, PA (US)

(72) Inventors: David Hackam, Baltimore, MD (US); Chhinder P. Sodhi, Columbia, MD (US); Peter Wipf, Pittsburgh, PA (US)

(73) Assignees: The Johns Hopkins University, Baltimore, MD (US); University of Pittsburgh—of the Commonwealth System of Higher Education, Pittsburgh, PA (US)

(*) Notice: Subject to any disclaimer, the term of this patent is extended or adjusted under 35 U.S.C. 154(b) by 49 days.

(21) Appl. No.: 16/854,196

(22) Filed: Apr. 21, 2020

(65) Prior Publication Data
US 2021/0128594 A1 May 6, 2021

Related U.S. Application Data

(63) Continuation of application No. 15/996,383, filed on Jun. 1, 2018, now Pat. No. 10,668,092, which is a continuation-in-part of application No. 15/383,625, filed on Dec. 19, 2016, now Pat. No. 10,300,083, which is a continuation of application No. 14/717,349, filed on May 20, 2015, now Pat. No. 9,532,999, which is a continuation of application No. 13/848,809, filed on Mar. 22, 2013, now Pat. No. 9,072,760, which is a continuation of application No. PCT/US2011/053293, filed on Sep. 26, 2011.

(60) Provisional application No. 61/386,345, filed on Sep. 24, 2010, provisional application No. 61/387,335, filed on Sep. 28, 2010.

(51) Int. Cl.
| | | |
|---|---|---|
| *A01N 43/04* | (2006.01) | |
| *A61K 31/70* | (2006.01) | |
| *A61K 31/7024* | (2006.01) | |
| *A61K 31/7028* | (2006.01) | |
| *A61K 31/7034* | (2006.01) | |
| *A61K 31/7008* | (2006.01) | |

(52) U.S. Cl.
CPC ...... *A61K 31/7024* (2013.01); *A61K 31/7008* (2013.01); *A61K 31/7028* (2013.01); *A61K 31/7034* (2013.01)

(58) Field of Classification Search
None
See application file for complete search history.

(56) References Cited

U.S. PATENT DOCUMENTS

| | | |
|---|---|---|
| 4,357,322 A | 11/1982 | Rooks, II et al. |
| 5,506,204 A | 4/1996 | Aston |
| 5,756,718 A | 5/1998 | Christ et al. |
| 5,962,636 A | 10/1999 | Bachmaier et al. |
| 6,034,230 A | 3/2000 | Bachmaier et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,406,705 B1 | 6/2002 | Davis et al. |
| 6,429,199 B1 | 8/2002 | Krieg et al. |
| 6,544,518 B1 | 4/2003 | Friede et al. |
| 6,558,670 B1 | 5/2003 | Friede et al. |
| 6,613,751 B2 | 9/2003 | Raz et al. |
| 6,652,392 B2 | 11/2003 | Higuchi et al. |
| 7,038,029 B2 | 5/2006 | Lopez |
| 7,049,302 B1 | 5/2006 | Kensil |
| 7,129,222 B2 | 10/2006 | Van Nest et al. |
| 7,183,111 B2 | 2/2007 | Van Nest et al. |
| 7,250,397 B2 | 7/2007 | Larsen et al. |
| 7,348,316 B2 | 3/2008 | Rossignol et al. |
| 7,744,884 B2 | 6/2010 | Elson |
| 7,851,451 B2 | 12/2010 | Clandinin et al. |
| 7,928,132 B2 | 4/2011 | Kohn et al. |
| 8,188,058 B2 | 5/2012 | Hackam et al. |
| 8,518,903 B2 | 8/2013 | Hackam |
| 8,518,905 B2 | 8/2013 | Hackam et al. |
| 9,072,760 B2 | 7/2015 | Wipf et al. |
| 9,353,061 B2 | 5/2016 | Lin et al. |
| 9,532,999 B2 | 1/2017 | Wipf et al. |
| 9,549,980 B2 | 1/2017 | Hackam |

(Continued)

FOREIGN PATENT DOCUMENTS

| | | |
|---|---|---|
| JP | 01-180894 | 7/1989 |
| WO | WO 98/18810 A1 | 5/1998 |

(Continued)

OTHER PUBLICATIONS

Cai et al. Organic Letters (2005), vol. 7, pp. 4021-4024.*

(Continued)

*Primary Examiner* — Patrick T Lewis
(74) *Attorney, Agent, or Firm* — Baker Botts L.L.P.

(57) ABSTRACT

The present invention relates to methods of treating infectious, inflammatory and post-traumatic disorders by administering various compounds newly discovered to have TLR4 inhibitory activity. In addition to methods of treatment, the present invention further provides for pharmaceutical compositions comprising said compounds, together with a suitable pharmaceutical carrier.

16 Claims, 12 Drawing Sheets

Specification includes a Sequence Listing.

(56) References Cited

U.S. PATENT DOCUMENTS

| | | | |
|---|---|---|---|
| 9,562,066 | B2 | 2/2017 | Hackam |
| 9,822,353 | B2 | 11/2017 | Buechler et al. |
| 2002/0064515 | A1 | 5/2002 | Krieg et al. |
| 2005/0250726 | A1 | 11/2005 | Krieg et al. |
| 2006/0211752 | A1 | 9/2006 | Kohn et al. |
| 2006/0241040 | A1 | 10/2006 | Visintin et al. |
| 2007/0004654 | A1 | 1/2007 | Raz et al. |
| 2008/0311112 | A1 | 12/2008 | Hackam et al. |
| 2009/0010902 | A1 | 1/2009 | Masuda |
| 2009/0215710 | A1 | 8/2009 | Upadhyay et al. |
| 2012/0077868 | A1 | 3/2012 | Hackam et al. |
| 2013/0072547 | A1 | 3/2013 | Hackam et al. |
| 2013/0281395 | A1 | 10/2013 | Wipf et al. |
| 2013/0345154 | A1 | 12/2013 | Hackam |
| 2014/0086982 | A1 | 3/2014 | Hackam |
| 2014/0377238 | A1 | 12/2014 | Budelli et al. |
| 2015/0056217 | A1 | 2/2015 | Hackam |
| 2017/0009549 | A1 | 1/2017 | Bhatnagar |
| 2017/0119897 | A1 | 5/2017 | Hackam et al. |

FOREIGN PATENT DOCUMENTS

| | | |
|---|---|---|
| WO | WO 3818810 | 5/1998 |
| WO | WO 98/37919 A1 | 9/1998 |
| WO | WO 3837919 | 9/1998 |
| WO | WO 98/52581 A1 | 11/1998 |
| WO | WO 3852581 | 11/1998 |
| WO | WO 99/33488 A2 | 7/1999 |
| WO | WO 3933488 | 7/1999 |
| WO | WO 00/61555 A1 | 10/2000 |
| WO | WO 3061555 | 10/2000 |
| WO | WO 2004/096156 | 11/2004 |
| WO | WO 2006/092049 | 9/2006 |
| WO | WO 2007/106886 | 9/2007 |
| WO | WO 2007/120368 | 10/2007 |
| WO | WO 2008/131074 | 10/2008 |
| WO | WO 2014/052453 | 4/2014 |
| WO | WO 2014/052453 A1 | 4/2014 |
| WO | WO 2018/027179 | 2/2018 |

OTHER PUBLICATIONS

U.S. Appl. No. 12/104,816 (U.S. Pat. No. 8,188,058), filed Apr. 17, 2008 (May 29, 2012).
U.S. Appl. No. 13/068,553 (U.S. Pat. No. 8,518,903), filed May 13, 2011 (Aug. 27, 2013).
U.S. Appl. No. 13/461,672 (U.S. Pat. No. 8,518,905), filed May 1, 2012 (Aug. 27, 2013).
U.S. Appl. No. 13/848,809 (U.S. Pat. No. 9,072,760), filed Mar. 22, 2013 (Jul. 7, 2015).
U.S. Appl. No. 13/921,865 (U.S. Pat. No. 10,172,848), filed Jun. 19, 2013 (Jan. 8, 2019).
U.S. Appl. No. 14/036,960 (U.S. Pat. No. 9,562,066), filed Sep. 25, 2013 (Feb. 7, 2017).
U.S. Appl. No. 14/010,232 (U.S. Pat. No. 9,549,980), filed Aug. 26, 2013 (Jan. 24, 2017).
U.S. Appl. No. 14/717,349 (U.S. Pat. No. 9,532,999), filed May 20, 2015 (Jan. 3, 2017).
U.S. Appl. No. 15/383,625 (U.S. Pat. No. 10,300,083), filed Dec. 19, 2016 (May 28, 2019).
U.S. Appl. No. 15/996,383 (U.S. Pat. No. 10,668,092), filed Jun. 1, 2018 (Jun. 2, 2020).
U.S. Appl. No. 12/104,816, filed May 14, 2013 Certificate of Correction.
U.S. Appl. No. 12/104,816, filed Apr. 23, 2012 Issue Fee payment.
U.S. Appl. No. 12/104,816, filed Jan. 23, 2012 Notice of Allowance.
U.S. Appl. No. 12/104,816, filed Nov. 10, 2011 Amendment and Request for Continued Examination (RCE).
U.S. Appl. No. 12/104,816, filed May 10, 2011 Final Office Action.
U.S. Appl. No. 12/104,816, filed Feb. 24, 2011 Response to Non-Final Office Action.
U.S. Appl. No. 12/104,816, filed Nov. 24, 2010 Non-Final Office Action.
U.S. Appl. No. 12/104,816, filed Sep. 15, 2010 Response to Restriction Requirement.
U.S. Appl. No. 12/104,816, filed Aug. 9, 2010 Restriction Requirement.
U.S. Appl. No. 13/068,553, filed Jul. 25, 2013 Issue Fee payment.
U.S. Appl. No. 13/068,553, filed Apr. 30, 2013 Notice of Allowance.
U.S. Appl. No. 13/068,553, filed Apr. 12, 2013 Reponse to Non-Final Office Action.
U.S. Appl. No. 13/068,553, filed Jan. 15, 2013 Non-Final Office Action.
U.S. Appl. No. 13/461,672, filed Jul. 25, 2013 Issue Fee payment.
U.S. Appl. No. 13/461,672, filed Apr. 29, 2013 Notice of Allowance.
U.S. Appl. No. 13/461,672, filed Apr. 12, 2013 Reponse to Non-Final Office Action.
U.S. Appl. No. 13/461,672, filed Jan. 14, 2013 Non-Final Office Action.
U.S. Appl. No. 13/848,809, filed May 12, 2015 Issue Fee Payment.
U.S. Appl. No. 13/848,809, filed Feb. 17, 2015 Notice of Allowance.
U.S. Appl. No. 13/848,809, filed Feb. 3, 2015 Request for Continued Examination (RCE).
U.S. Appl. No. 13/848,809, filed Nov. 10, 2014 Notice of Allowance.
U.S. Appl. No. 13/921,865, filed Nov. 16, 2018 Issue Fee Payment.
U.S. Appl. No. 13/921,865, filed Aug. 16, 2018 Notice of Allowance.
U.S. Appl. No. 13/921,865, filed Aug. 6, 2018 Response after Final Action.
U.S. Appl. No. 13/921,865, filed Jun. 7, 2018 Final Office Action.
U.S. Appl. No. 13/921,865, filed Feb. 14, 2018 Response to Non-Final Office Action.
U.S. Appl. No. 13/921,865, filed Nov. 14, 2017 Non-Final Office Action.
U.S. Appl. No. 13/921,865, filed Nov. 8, 2016 Amendment and Request for Continued Examination (RCE).
U.S. Appl. No. 13/921,865, filed Aug. 8, 2016 Final Office Action.
U.S. Appl. No. 13/921,865, filed Apr. 25, 2016 Response to Non-Final Office Action.
U.S. Appl. No. 13/921,865, filed Jan. 25, 2016 Non-Final Office Action.
U.S. Appl. No. 13/921,865, filed Aug. 11, 2015 Amendment and Request for Continued Examination (RCE).
U.S. Appl. No. 13/921,865, filed Mar. 11, 2015 Final Office Action.
U.S. Appl. No. 13/921,865, filed Nov. 14, 2014 Response to Non-Final Office Action.
U.S. Appl. No. 13/921,865, filed Aug. 14, 2014 Non-Final Office Action.
U.S. Appl. No. 13/921,865, filed Jul. 10, 2014 Response to Non-Final Office Action.
U.S. Appl. No. 13/921,865, filed Mar. 12, 2014 Non-Final Office Action.
U.S. Appl. No. 13/921,865, filed Nov. 27, 2013 Response to Restriction Requirement.
U.S. Appl. No. 13/921,865, filed Sep. 27, 2013 Restriction Requirement.
U.S. Appl. No. 14/036,960, filed Dec. 21, 2016 Issue Fee Payment.
U.S. Appl. No. 14/036,960, filed Oct. 26, 2016 Notice of Allowance.
U.S. Appl. No. 14/036,960, filed Jul. 20, 2016 Response to Non-Final Office Action.
U.S. Appl. No. 14/036,960, filed Apr. 20, 2016 Non-Final Office Action.
U.S. Appl. No. 14/036,960, filed Jan. 4, 2016 Response to Non-Final Office Action.
U.S. Appl. No. 14/036,960, filed Oct. 1, 2015 Non-Final Office Action.
U.S. Appl. No. 14/036,960, filed Jul. 9, 2015 Response to Non-Final Office Action.
U.S. Appl. No. 14/036,960, filed Jan. 12, 2015 Non-Final Office Action.
U.S. Appl. No. 14/036,960, filed Dec. 22, 2014 Response to Restriction Requirement.

(56) References Cited

OTHER PUBLICATIONS

U.S. Appl. No. 14/036,960, filed Sep. 23, 2014 Restriction Requirement.
U.S. Appl. No. 14/010,232, filed Nov. 23, 2016 Issue Fee Payment.
U.S. Appl. No. 14/010,232, filed Sep. 28, 2016 Notice of Allowance.
14/010,232, filed Aug. 10, 2016 Amendment and Request for Continued Examination (RCE).
U.S. Appl. No. 14/010,232, filed May 10, 2016 Final Office Action.
U.S. Appl. No. 14/010,232, filed Sep. 21, 2015 Response to Non-Final Office Action.
U.S. Appl. No. 14/010,232, filed Jun. 19, 2015 Non-Final Office Action.
U.S. Appl. No. 14/010,232, filed May 27, 2015 Response to Restriction Requirement.
U.S. Appl. No. 14/010,232, filed Feb. 27, 2015 Restriction Requirement.
U.S. Appl. No. 17/717,349, filed Nov. 22, 2016 Issue Fee Payment.
U.S. Appl. No. 14/717,349, filed Aug. 29, 2016 Notice of Allowance.
U.S. Appl. No. 14/717,349, filed Aug. 15, 2016 Response after Final Office Action.
U.S. Appl. No. 14/717,349, filed May 26, 2016 Final Office Action.
U.S. Appl. No. 14/717,349, filed Mar. 10, 2016 Response to Non-Final Office Action.
U.S. Appl. No. 14/717,349, filed Dec. 10, 2015 Non-Final Office Action.
U.S. Appl. No. 15/996,383, filed Apr. 21, 2020 Issue Fee Payment.
U.S. Appl. No. 15/996,383, filed Mar. 31, 2020 Notice of Allowance.
U.S. Appl. No. 15/996,383, filed Jan. 21, 2020 Notice of Allowance.
U.S. Appl. No. 15/996,383, filed Oct. 17, 2019 Response to Non-Final Office Action.
U.S. Appl. No. 15/996,383, filed Jul. 15, 2019 Non-Final Office Action.
U.S. Appl. No. 15/383,625, filed Apr. 9, 2019 Issue Fee Payment.
Abreu et al., 2005, "TLR Signaling in the Gut in Health and Disease." J Immunol 174:4453-4460.
Achkar, "Ulcerative colitis: Responding to the challenges", Cleveland Clinic J. Med., 2007; 74(9):657-660.
Afrazi et al. "New insights into the pathogenesis and treatment of necrotizing enterocolitis: Toll-like receptors and beyond", Pediatr Res., 2011; 69:183-188.
Afrazi et al., "Intracellular heat shock protein—70 negatively regulates TLR4 signaling in the newborn intestinal epithelium", J. Immunol., 2012, 188:4543-4557.
Aki Tsukioka, "Eisai Successfully Completes Phase II Trial of Eritoran, Drug Candidate for Severe Sepsis." JCN Network, Aug. 30, 2005 p. 1. Downloaded on Nov. 20, 2009 from http://www.japancorp.net/printarticle.asp?Art_ID= 10765.
Amer et al., "Platelet-activating factor concentration in the stool of human newborns: effects of enteral feeding and neonatal necrotizing enterocolitis", Biol Neonate, 2004; 85:159-166.
Anand et al., 2007, "The Role of the Intestinal Barrier in the Pathogenesis of Necrotizing Enterocolitis." Shock 27:124-133.
U.S. Appl. No. 15/383,625, filed Jan. 9, 2019 Notice of Allowance.
U.S. Appl. No. 15/383,625, filed Oct. 18, 2018 Response to Non-Final Office Action.
U.S. Appl. No. 15/383,625, filed Jul. 19, 2018 Non-Final Office Action.
U.S. Appl. No. 15/383,625, filed Apr. 11, 2018 Response to Non-Final Office Action.
U.S. Appl. No. 15/383,625, filed Jan. 11, 2018 Non-Final Office Action.
Anderson, 2001, "Infant, neonatal, and postnatal deaths, percent of total deaths, and mortality rates for the 10 leading muses of infant death by race and sex: United States: 1999." National Vital Statistics Reports. 49:73.

Arciero et al., "Modeling the interactions of bacteria and Toll-like receptor-mediated in-flammation in necrotizing enterocolitis," Journal of Theoretical Biology 321:83-99 (2013).
Berge et al., Pharmaceutical Salts., J. Pharm. Sci., 66: 1-19 (1977).
Blakely et al., "Postoperative outcomes of extremely low birth-weight infants with necrotizing enterocolitis or isolated Intestinal perforation: a prospective cohort study by the NICHD Neonatal Research Network", Ann Surz. 2005; 241 ;6):984-989.
Borges et al., "Immune response by nasal delivery of hepatitis B surface and antigen and codelivery of a CpG ODN in alginate coated chitosan nanoparticles", European Journal of Pharmaceutics and Biopharmaceutics, 59:405-416 (2008).
Borzutzky et al., "NOD2-associated diseases: Bridging innate immunity and autoinflammation", Clin Immunol., 2010; 134:251-261.
Caplan et al., "Neonatal necrotizing entercolitis: possible role of probiotic supplementation", Journal of Pediatric Gastroenterology and Nutrition, 30(2): S18-S22 (2000).
Caplan et al., "The platelet activating factor receptor antagonist WEB 2170 prevents neonatal necrotizing enterocolitis n rats", J Pediatr Gastroenterol Nutr. 1997; 24:296-301.
Caplan et al., "The role of recombinant platelet activating factor acetylhydrolase in a neonatal rat model of necrotizing enterocolitis", Pediatr Res., 1997; 42:779-783.
Caradonna et al., "Phagocytosis, killing, lymphocyte-mediated antibacterial activity, serum autoantibodies, and plasma endotoxins in inflammatory bowel disease", Am J Gastroenterol. 2000; 95: 1495-1502.
Career Opportunities—Eisai announces Phase II results, plans to initiate phase III clinical—Aug. 29, 2005. Downloaded on Apr. 18, 2007 from http://www.eisai.com/view_pressrelease. asp?ID=145 &press=124.
Cario et al., 2000, "Lipopolysaccharide activates distinct signaling pathways in intestinal epithelial cell lines expressing Toll-like receptors." J Immunol. 164(2):966-72.
Carneiro et al., 2008, "Nod-like proteins in inflammation and disease." J Pathol. 214(2):136-48.
Cavallo et al., 2006 "The expression and function of enterocyte toll like receptor-4 are enhanced by lipopolysaccharide in vitro and during systemic endotoxemia." Association for academic surgery and society of university surgeons—Abstracts. Journal of Surgical Research vol. 130, Issue 2, p. 232, No. 189.
Cetin et al., 2004, "Endotoxin inhibits intestinal epithelial restitution through activation of Rho-GTPase and increased focal adhesions." J Biol Chem. 279(23):24592-600. Epub Mar. 30, 2004.
Cetin et al., 2007, "Nitric oxide inhibits enterocyte migration through activation of RhoA-GTPase in a SHP-2-dependent manner." Am J Physiol Gastrointest Liver Physiol 292:G1347-1358.
Chan et al., "Role of LPS/CD 14/TLR4-mediated inflammation in necrotizing enterocolitis: pathogenesis and therapeutic implications", World J Gastroenterol., 2009; 15:4745-4752.
Cho et al., 2007, "The genetics of inflammatory bowel disease." Gastroenterology 133:1327-1339.
Creagh et al., 2006, "TLRs, NLRs and RLRs: a trinity of pathogen sensors that co-operate in innate immunity." Trends Immunol. 27(8):3 52-7. Epub Jun. 27, 2006.
Dai et al., "Extracellular high mobility group box I (HMGBI) inhibits enterocyte migration via activation of toll like-receptor 4 and increased cell-matrix adhesiveness", J Biol Chem., 2010; 285:4995-5002.
Daubenberger, 2007, "TLR9 agonists as adjuvants for prophylactic and therapeutic vaccines." Curr. Opin. Molec. Ther. 9:45-52.
Ding et al., 1998, "Characterization and quantitation of NF-kappaB nuclear translocation induced by interleukin-I and tumor necrosis factor-alpha. Development and use of a high capacity fluorescence cytometric system." J Biol Chem. 273(44):28897-905.
Diwan et al., "Enhancement of immune responses by co-delivery of a CpG oligodeoxynucleotide and tetanus toxoid in Biodegradable nanospheres", J. Control Release, 85(1-3):247-262 (2002).
Duffy et al., "Concordance of bacterial cultures with endotoxin and interleukin-6 in necrotizing enterocolitis", Di Dis Sci. 1997; 42:359-365.

(56) References Cited

OTHER PUBLICATIONS

Ewaschuk et al., 2007, "Surface expression of Toll-like receptor 9 is upregulated on intestinal epithelial cells in-response to pathogenic bacterial DNA." Infect Immun. 75(5) 2572-9. Epub Feb. 26, 2007.
Ey et al., "TLR2 mediates gap junctional intercellular communication through connexin-43 in intestinal epithelial barrier injury", The Journal of Biological Chemistry, 284:22332-22343 (2009).
Feng et al., "Heparin-binding epidermal growth factor-like growth factor promotes enterocyte migration and proliferation n neonatal rats with necrotizing enterocolitis", J Pediatr Surz., 2007; 42:214-220.
Feng et al., 2005, "Heparin-binding EGF-like growth factor (HB-EGF) and necrotizing enterocolitis." Semin Pediatr Surg. 14(3):167-74.
Franchi et al., 2008, "Intracellular NOD-like receptors in innate immunity, infection and disease." Cell Microbiol 10:1-8.
Fukata et al., "Cox-2 is regulated by Toll-like receptor-4 (TLR4) signaling: Role in proliferation and apoptosis in the intestine", Gastroenterology, 2006; 131:862-877.
Fukata et al., "Innate immune signaling by Toll-like receptor-4 (TLR4) shapes the inflammatory microenvironment in colitis-associated tumors", Inflamm Bowel Dis. 2009; 15:997-1006.
Fukata et al., "TLR4 signaling in the intestine in health and disease", Biochemical Society Transactions, 3 5 ;6):1473-1478 (2007).
Fukata et al., "Toll-like receptor-4 is required for intestinal response to epithelial injury and limiting bacterial translocation in a murine model of acute colitis", Am J Physiol Gastrointest Liver Physiol., 2005; 288:G1055-G1065.
Gagliardi et al., "Necrotising enterocolitis in very low birth weight infants in Italy: incidence and non-nutritional risk actors", J. Pediatr Gastroenterol Nutr., 2008; 47(2)206-210.
Good et al., "Evidence based feeding strategies before and after the development of necrotizing enterocolitis," Expert Rev Clin Immunol., Jul. 2014; 10(7):875-884.
Goodenough, "Bulk isolation of mouse hepatocyte gap junctions. Characterization of the principal protein connexin", J. Cell Biol., 1974; 61: 557-563.
Goodenough, "The structure of cell membranes involved in intercellular communication", Am. J. Clin. Pathol., 1975; 33:636-645.
Grave et al., "New therapies and preventive approaches for necrotizing enterocolitis: report of a research planning workshop", Pediatr Res., 2007; 62:510-514.
Gribar et al., "Reciprocal expression and signaling of TLR4 and TLR9 in the pathogenesis and treatment of necrotizing entercolitis", Journal of Immunologists, 182(1):636-646 (2009).
Gribar et al., 2008, "The role of epithelial Toll-like receptor signaling in the pathogenesis of intestinal inflammation." J Leukoc Biol. 83(3):493-8. Epub Dec. 26, 2007.
Grimm et al., "NOD2 Mutations and Crohn's Disease: Are Paneth Cells And Their Antimicrobial Peptides The Link?" Gut; 53(11): 1558-1560, Nov. 2004.
Gudmundsdottir et al., Organic Letters (2008), vol. 10, pp. 3461-3463.
Guthrie et al., 2003, "Necrotizing enterocolitis among neonates in the United States." J.
Hackam et al., "Mechanisms of gut barrier failure in the pathogenesis of necrotizing enter-ocolitis: toll like receptors throw the switch," Semin Pediatr Surg 22(2):76-82 (2013).
Halpern et al., 2006, "Reduction of experimental necrotizing enterocolitis with anti-TNF-a." Am J. Physiol Gastrointest Liver Physiol 290, pp. G757-G764.
Henckaerts et al., "NOD/CARD15 Disease Associations Other Than Crohn's disease," In-flamm Bowel Dis 13:235-241 (2007).
Henry et al., 2005, "Surgical therapy for necrotizing enterocolitis: bringing evidence to the bedside." Semin Pediatr Surg. 14(3):181-90.
Henry et al., 2006, "Laparotomy Versus Peritoneal Drainage for Perforated Necrotizing Enterocolitis." Neoreviews 7:456-462.
Hotta et al., "Lipopolysaccharide-induced colitis in rabbits", Res Exp Med (Bed) 1986; 186:61-69.

Hsueh et al., 2003 "Neonatal necrotizing enterocolitis: clinical considerations and pathogenetic concepts." Pediatr Dev Pathol 6:6-23.
Hugot et al., "Association of NOD2 leucine-rich repeat variants with susceptibility to Crohn's disease." Nature. 411 6837):599-603 (2001).
I EC-6 cells, Sigma Aldrich, accessed Aug. 2, 2016 at URL sigmaal-drich.com/catalog/product/sigma/88071401, 1 page.
International Search Report for PCT/US2011/053293, dated Apr. 9, 2012.
InvivoGen: Delivering Genes. "TLR9 Ligands." Downloaded on Apr. 16, 2007 from STFhrrp://www.invivogen.com/family.php?ID-1048LID cat-2&ID sscat-9.
Iwasaki et al., "Regulation of adaptive immunity by the innate immune system", Science, 2010; 327:291-295.
Izumi et al., "Platelet-activating factor receptor: gene expression and signal transduction", Biochim Biophys Acta, 1995; 1259:317-333.
Jesse et al., 2006, "Necotrizing enterocolitis: Relationship to Innate Immunity, Clinical Features, and Strategies for prevention." NeoReviews 7: 143-150.
Jilling et al., "The roles of bacteria and TLR4 in rat and murine models of necrotizing enterocolitis." J Immunol. 177 5):3273-82 (2006).
Kanneganti et al., 2007, "Intracellular NOD-like receptors in host defense and disease." Immunity 27:549-559.
Katakura et al., "Toll-like receptor 9-induced type I IFN protects mice from experimental colitis." J Clin Invest. 115(3):695-702. Erratum in: J Clin Invest. 2005 115(4): 1100 (2005).
Kitagaki et al., "Oral administration of CpG-ODNs suppresses antigen-induced asthma in mice", British Society for Immunology, Clinical and Experimental Immunology, 143:249-259 (2005).
Knapp, et al., "Thiomation: GIcNAc-Thiazoline Triacetate r(3Ar,5R,6S,7R,7aR)-5-Acetoxymethyl-6, 7-Diacetoxy-2-Methyl-5,6, 7,7a-Tetrahydro-3aH-Pyrano 3,2-d]Thiazole} ", Organic Syntheses, 84:68-76 (2007).
Kobayashi et al., "Suppression of murine endotoxin response by E5531, a novel synthetic lipid A antagonist." Antimicrob Agents Chemother. 42(11):2824-9 (1998).
Kosloske, 1994, "Epidemiology of necrotizing enterocolitis." Acta Pediatr. Suppl. 396:2-7.
Krieg, 2006, "Therapeutic potential of Toll-like receptor 9 activation." Nat. Rev. Drug Disc. 5:471-484.
Kruis et al., "Circulating lipid A antibodies despite absence of systemic endotoxemia in patients with Crohn's disease", Diz Dis Sci., 1984; 29:502-507.
Laird, "Connexin phosphorylation as a regulatory event linked to gap junction internalization and degradation", Biochi. 3iophys. Acta, 2005; 1711:172-182.
Lampe et al., "Phosphorylation of connexin-43 on serine 368 by protein kinase C regulates gap junction communication", J Cell Biol., (2000) 149:1503-1512.
Lavelle et al., "The role of TLRs, NLRs, and RLRs in mucosal innate immunity and ho-meostasis," Mucosal Immunol 3(1):17-28 (2010).
Leapart et al., "Interferon-γ inhibits enterocyte migration by reversibly displacing connexion43 from lipid rafts", Am Physiol Gastrointest Liver Physiol, 2008; 295:G559-G569.
Leaphart et al., 2007, "Interferon-gamma inhibits intestinal restitution by preventing gap junction communication between enterocytes." Gastroenterology. 132(7):2395-411. Epub Mar. 21, 2007.
Leaphart et al., 2007. "A Critical Role for TLR4 in the Pathogenesis of Necrotizing Enterocolitis by Modulating Intestinal injury and Repair." J Immunology 179:4808-4820.
Lee et al., 2006, "Homeostatic effects of TLR9 signaling in experimental colitis." Ann N Y Arad Sci. 1072:351-5.
Lemaitre et al., "The dorsoventral regulatory gene cassette spatzle/Toll/cactus controls the potent antifungal response in Drosophila adults", Cell, 1996; 86:973-983.
Lin et al., "Oral probiotics reduce the incidence and severity of necrotizing enterocolitis in very low birth weight infants", Pediatrics, 2005; 115:1-4.
Lin et al., 2006, "Necrotising enterocolitis." Lancet 368:1271-1283.

(56) References Cited

OTHER PUBLICATIONS

Liu et al., "Changes in intestinal toll-like receptors and cytokines precede histological injury in a rat model of necrotizing enterocolitis", Am JPhysiol Gastrointest Liver Physiol., 2009; 297:G442-G450.

Lotz et al., "Postnatal acquisition of endotoxin tolerance in intestinal epithelial cells", JExp Med., 2006; 203 :973-984.

Lu et al., "Polyunsaturated fatty acid supplementation alters proinflammatory gene expression and reduces the incidence of necrotizing enterocolitis in a neonatal rat model", Pediatr Res., 2007; 61:427-432.

Luig et al., "Epidemiology of necrotizing enterocolitis—Part1: Changing regional trends in extremely preterm infants over 14 years", J Paediatr Child Health, 2005; 41(4): 169-73.

Macagno et al., 2006, "A cyanobacterial LPS antagonist prevents endotoxin shock and blocks sustained TLR4 stimulation required for cytokine expression." J. Exp. Med. 203(6): 1481-1492.

Maeda et al., 2005, "Nod2 mutation in Crohn's disease potentiates NF-kappaB activity and IL-Ibeta processing." Science 307:734-738. Erratum in Science. Apr. 29, 2005;308(5722):633.

Medzhitov et al., "A human homologue of the *Drosophila* Toll protein signals activation of adaptive immunity", Nature, 1997; 388:394-397.

Merck Manual website, Nov. 2007 by William J. Cochran, MD. Downloaded on Nov. 7, 2011 from <http://www.merckmanuals.com/professional/pediatrics/gastrointestinal_disorders_in_neon ates_and_infants/necrotizing_enterocolitis.html>.

Michaelsson et al., "Regulation of T cell responses in the developing human fetus", J Immunol., 2006; 176 ;10):5741-5748.

Milla et al., "Small intestinal motility patterns in the perinatal period", JPediatr. Gastroenterol Nutr., 1983;2:S141-S144.

Mizrahi et al., "Necrotizing enterocolitis in premature infants", J Pediatr., 1965; 66:697-705.

Moss et al., 2006, "Laparotomy versus peritoneal drainage for necrotizing enterocolitis and perforation." N. Engl. J. Med. 354:2225-2234.

Muguruma et al., "The central role of PAF in necrotizing enterocolitis development", Adv Exv Med Biol. 1997; 107:379-382.

Mullarkey et al., 2003, "Inhibition of endotoxin response by e5564, a novel Toll-like receptor 4-directed endotoxin antagonist." J Pharmacol Exp Ther. 304(3): 1093-102.

Neal et al., "A critical role for TLR4 induction of autophagy in the regulation of enterocyte migration and the pathogenesis of necrotizing enterocolitis", J. Immunol., 2013; 190(7):3541-3551.

Neal et al., "Enterocyte TLR4 mediates phagocytosis and translocation of bacteria across the intestinal barrier." J Immunol. 176(5):3070-9 (2006).

Neu et al., 2005, "Intestinal innate immunity: how does it relate to the pathogenesis of necrotizing enterocolitis." Semin. Pediatr. Surg. 14: 137-144.

Neu, 1996, "Necrotizing enterocolitis: the search for a unifying pathogenic theory leading to prevention." Pediatr Clin North Am. 43(2):409-32.

Ng, 2001, "Necrotizing enterocolitis in the full-term neonate." J Paediatr Child Health. 37(1):1-4.

Noerr, "Current controversies in the understanding of necrotizing enterocolitis", Adv Neonatal Care, 2003; 3:107-120.

Obermeier et al. 2002, "CpG motifs of bacterial DNA exacerbate colitis of dextran sulfate sodium-treated mice." Eur J Immunol. Jul. 2002;32(7):2084-92.

Obermeier et al., "Contrasting activity of cytosin-guanosin dinucleotide oligonucleotides in mice with experimental colitis", Clin Exp Immunol., 134(2):217-224 (2003).

Ogura et al., "A frameshift mutation in NOD2 associated with susceptibility to Crohn's disease." Nature. 411 (6837):603-6 (2001).

Otte et al., 2004, "Mechanisms of cross hyporesponsiveness to Toll-like receptor bacterial ligands in intestinal epithelial cells." Gastroenterology. 126(4):1054-70.

Panigrahi, "Necrotizing enterocolitis", Paediatr. Drugs, 2006; 8(3):151-165.

Parant et al., "Stimulation of Non-specific Resistance to Infections by Synthetic Immuno-regulatory Agents," Infection 12(3):230-234 (1984).

Pierro, 2005, "The surgical management of necrotising enterocolitis." Early Hum Dev. 81(1):79-85.

Poltorak et al., 1998, "Defective LPS Signaling in C3H/HeJ and C57BL/10ScCr Mice: Mutations in Tlr4 Gene." Science 282: 2085-2088.

Prohinar et al., "Specific high affinity interactions of monomeric endotoxin.protein complexes with Toll-like receptor 4 ectodomain." J Biol Chem. 282(2): 1010-7. (2007).

Putta et al., 2006, "Novel oligodeoxynucleotide agonists of TLR9 containing N3—Me—dC or NI—Me—dG modifications." gucleic Acids Res. 34(11):3231-8.

Qureshi et al., "Increased expression and function of integrins in enterocytes by endotoxin impairs epithelial-restitution", Gastroenterology, 2005; 128:1012-1022.

Rachmelewitz et al., 2004, "Toll-like receptor 9 signaling mediates the anti-inflammatory effects of probiotics in murine experimental colitis." Gastroenterology. 126(2):520-8.

Rakoff-Nahoum et al., "Recognition of commensal microflora by toll-like receptors is required for intestinal homeostasis", Cell, 2004; 118:229-241.

Richardson, et al., "Nucleotide-binding Oligomerization Domain-2 Inhibits Toll Like Receptor-4 Signaling in the Intestinal Epithelium", Gastroenterology, 139(3):904-917 (2010).

Roach et al., "The evolution of vertebrate Toll-like receptors", PNAS, 2005; 102:9577-9582.

Rossignol et al., 2004, "Safety, pharmacokinetics, pharmacodynamics, and plasma lipoprotein distribution of eritoran E5564) during continuous intravenous infusion into healthy volunteers." Antimicrob Agents Chemother. 48(9):3233-40.

Sartor, "Targeting enteric bacteria in treatment of inflammatory bowel diseases: why, how, and when," Current Opinion in Gastroenterology 19:358-365 (2003).

Shan et al., "Regulation of toll-like receptor 4-induced proasthmatic changes in airway smooth muscle function by opposing actions of ERK 1/2 and p38 MAPK signaling", Am J Physiol. LunK Cell Mol. Physiol., 291(3):L324-L333) (2006).

Sharma et al., 2007, "Neonatal gut barrier and multiple organ failure: role of endotoxin and proinflammatory cytokines in sepsis and necrotizing enterocolitis." J Pediatr Surg 42:454-461.

Shin et al., 2000, "Diminished epidermal growth factor levels in infants with necrotizing enterocolitis." J Pediatr Surg. 35(2): 173-6; discussion 177.

Shindou et al., "Roles of cytosolic phospholipase A2 and platelet-activating factor receptor in the Ca-induced biosynthesis of PAF", Biochem Biophys Res Commun. 2000; 271 :812-817.

Shuto et al., "Activation of NF-kappa B by nontypeable hemophilus influenzae is mediated by toll-like receptor 2-TAK dependent NIK-IKK alpha/beta-I kappa B alpha and MKK3/6-p38 MAP kinase signaling pathways in epithelial cells", PNAS, 98(15) 8774-8779 (2001).

Sodhi, et al., "DNA Attenuates Enterocyte Toll-like Receptor 4-Mediated Intestinal Mucosa! Injury After Remote Trauma", Am J Physiol Gastrointest Liver Physiol., 300 G862-G873 (2011).

Sodhi, et al., "Toll-like-receptor-4 Inhibits Enterocyte Proliferation via Impaired—Catenin Signaling in Necrotizing Enterocolitis", Gastroenterology, 138(1):185-196 (2010).

Strober et al., 2006, "Signalling pathways and molecular interactions of NOD I and NOD2." Nat Rev Immunol. 6:9-20.

Supplemental European Search Report for EP Application No. 08746070.5, dated May 25, 2011.

Svetlov et al., "Regulation of platelet-activating factor (PAF) biosynthesis via coenzyme A-independent transacylase in the macrophage cell line IC-21 stimulated with lipopolvsaccharide", Biochim Biophvs Acta, 1997; 1346:120-130.

Takeda et al., "Toll-like receptors in innate immunity." Int Immunol. 17(1):1-14.

Takeda et al., 2001, "Roles of Toll-like receptors in innate immune responses." Genes Cells 6:733-742.

(56) References Cited

OTHER PUBLICATIONS

Tatum et al., "The role of toll-like receptor 9 in an animal model of necrotizing entercolitis", Journal of Investigative Medicine, 58(2):436 (2010).

Thai et al., "Cutting edge: TLR4 activation mediates liver ischemia/repertusion inflammatory response via IFN regulatory factor 3-dependent MyD88-independent pathway", J Immunol., 173(12):7115-7119 (2004).

Thompson et al., "Necrotizing enterocolitis in newborns", Drugs, 2008; 68(9): 1227-1238.

Uauy et al., 1991, "Necrotizing enterocolitis in very low birth weight infants: biodemographic and clinical correlates." National Institute of Child Health and Human Development Neonatal Research Network. J Pediatr 119:630-638.

University of Pittsburgh Department of Critical Care Medicine: Research—The Crisma Laboratory, pp. 1-11. Downloaded on Apr. 19, 2007 from http:/www.ccm.upmc.edu/research/rescrisma.htlm.

Van Heel et al., "Synergy between TLR9 and NOD2 innate immune responses is lost in genetic Chrohn's disease" GUT, British Medical Association, 54(11): 1553-1557 (2005).

Verma et al., "Novel pharmacophores of connexin-43 based on the "RXP" series of Cx43-binding peptides", Circ. Res., 2009; 105(2):176-184.

Verthelyi et al., "Human peripheral blood cells differentially recognize and respond to two distinct CPG motifs." J Immunol. 166(4):2372-7 (2001).

Vink et al., 2002, "In vivo evidence for a role of toll-like receptor 4 in the development of intimal lesions." Circulation. 106(15):1985-90.

Wang et al., "NF-KB-mediated expression of MAPK phosphatase-I is an early step in desensitization to TLR ligands in enterocytes", Mucosa! Immunol., 2010; 3 :523-534.

Wang et al., "Ubiquitin-editing enzyme A20 promotes tolerance to lipopolysaccharide in enterocytes", J Immunol., 2009; 183:1384-1392.

Warner et al., 2005, "Role of epidermal growth factor in the pathogenesis of neonatal necrotizing enterocolitis." Semin Pediatr Surg. 14(3):175-80.

Watanabe et al., "Muramyl dipeptide activation of nucleotide-binding oligomerization domain 2 protects mice from experimental colitis." J Clin Invest 118:545-559 (2008).

Watanabe et al., "Muramyl dipeptide activation of nucleotide-binding oligomerization domain 2 protects mice from experimental colitis," J Clin Invest 118(2):545-559 (2008).

Wirtz et al., "Illuminating the role of type I IFNs in colitis." J Clin Invest. 115(3):586-8 (2005).

Wolfs et al., "Localization of the lipopolysaccharide recognition complex in the human healthy and inflamed premature 3nd adult i:rut", Inflamm Bowel Dis., 2010; 16:68-75.

Worthen et al., "The priming of neutrophils by lipopolysaccharide for production of intracellular platelet-activating factor: potential role in mediation of enhanced superoxide secretion", J Immunol., 1988; 140:3553-3559.

Wynn et al., "The host response to sepsis and developmental impact", Pediatrics, 2010; 125:1031-1041.

Yang et al., "NOD2 transgenic mice exhibit enhanced MDP-mediated down-regulation of TLR2 responses and resistance to colitis induction." Gastroenterology 133:1510-1521 (2007).

Yang et al., 2005, "Role of Toll-like receptor 4/NF-kappaB pathway in monocyte-endothelial adhesion induced by low shear stress and ox-LDL." Biorheology. 42(3):225-236.

Yang et al., 2007, "NOD2 pathway activation by MDP or Mycobacterium tuberculosis infection involves the stable polyubiquitination of Rip2." J Biol Chem 282:36223-36229.

Yeung et al., Organic Letters (2000), vol. 2, pp. 3135-3138.

Zhai et al., "Cutting edge: TLR4 activation mediates liver ischemia/reperfusion inflammatory response via IFN regulatory factor 3-dependent MyD88-independent pathway", J Immunol., 173(12):7115-7119 (2004).

Zheng et al., "Regulation of colonic epithelial repair in mice by Toll-like receptors and hyaluronic acid", Gastroenterology V, 2009; 137:2041-2051.

Zhou et al., "Oral administration of plant-based rotavirus VP6 induces antigen-specific IgAs, IgGs and passive protection in mice" Vaccine, 28:6021-6027 (2010).

Zouali et al., "CARD15/NOD2 is Not a Predisposing Factor for Necrotizing Enterocolitis," Digestive Diseases and Sci 50(9):1684-1687 (2005).

\* cited by examiner

SEQUENCE LISTING

```
<160> NUMBER OF SEQ ID NOS: 16

<210> SEQ ID NO 1
<211> LENGTH: 24
<212> TYPE: DNA
<213> ORGANISM: Mus musculus

<400> SEQUENCE: 1
agtgtggatc ccaagcaata ccca                                            24

<210> SEQ ID NO 2
<211> LENGTH: 24
<212> TYPE: DNA
<213> ORGANISM: Mus musculus

<400> SEQUENCE: 2
tgtcctgacc actgttgttt ccca                                            24

<210> SEQ ID NO 3
<211> LENGTH: 24
<212> TYPE: DNA
<213> ORGANISM: Rattus norvegicus

<400> SEQUENCE: 3
ctgctggtgg tgacaagcac attt                                            24

<210> SEQ ID NO 4
<211> LENGTH: 24
<212> TYPE: DNA
<213> ORGANISM: Rattus norvegicus

<400> SEQUENCE: 4
atgtcatgag caaaggcgca gaac                                            24

<210> SEQ ID NO 5
<211> LENGTH: 21
<212> TYPE: DNA
<213> ORGANISM: Mus musculus

<400> SEQUENCE: 5
acaaccagtt cgccatggta t                                               21

<210> SEQ ID NO 6
<211> LENGTH: 20
```

```
<212> TYPE: DNA
<213> ORGANISM: Mus musculus

<400> SEQUENCE: 6
aagcgggtga aacgttcctt                                             20

<210> SEQ ID NO 7
<211> LENGTH: 24
<212> TYPE: DNA
<213> ORGANISM: Mus musculus

<400> SEQUENCE: 7
gacagtgtca gagatgaagc tact                                        24

<210> SEQ ID NO 8
<211> LENGTH: 21
<212> TYPE: DNA
<213> ORGANISM: Mus musculus

<400> SEQUENCE: 8
ttgatgcttt ctctccgctc c                                           21

<210> SEQ ID NO 9
<211> LENGTH: 20
<212> TYPE: DNA
<213> ORGANISM: Mus musculus

<400> SEQUENCE: 9
gcagtacgag cggcggagac                                             20

<210> SEQ ID NO 10
<211> LENGTH: 21
<212> TYPE: DNA
<213> ORGANISM: Mus musculus

<400> SEQUENCE: 10
gggcgggtgt aggcacctag t                                           21

<210> SEQ ID NO 11
<211> LENGTH: 24
<212> TYPE: DNA
<213> ORGANISM: Mus musculus

<400> SEQUENCE: 11
ttccgaattc actggagcct cgaa                                        24

<210> SEQ ID NO 12
<211> LENGTH: 24
<212> TYPE: DNA
<213> ORGANISM: Mus musculus

<400> SEQUENCE: 12
tgcacctcag ggaagaatct ggaa                                        24

<210> SEQ ID NO 13
<211> LENGTH: 25
<212> TYPE: DNA
<213> ORGANISM: Rattus norvegicus

<400> SEQUENCE: 13
catcttctca aaattcgagt gacaa                                       25

<210> SEQ ID NO 14
```

```
<211> LENGTH: 23
<212> TYPE: DNA
<213> ORGANISM: Rattus norvegicus

<400> SEQUENCE: 14
tgggagtaga caaggtacaa ccc                                              23

<210> SEQ ID NO 15
<211> LENGTH: 20
<212> TYPE: DNA
<213> ORGANISM: Rattus norvegicus

<400> SEQUENCE: 15
ggcgacctgg aagtccaact                                                  20

<210> SEQ ID NO 16
<211> LENGTH: 20
<212> TYPE: DNA
<213> ORGANISM: Rattus norvegicus

<400> SEQUENCE: 16
ccatcagcac cacagccttc                                                  20
```

COMPOSITIONS AND METHODS FOR TREATMENT OF INFLAMMATORY DISORDERS

REFERENCE TO RELATED APPLICATIONS

This application is a continuation of U.S. patent application Ser. No. 15/996,383, filed Jun. 1, 2018, which is a continuation-in-part of U.S. patent application Ser. No. 15/383,625, filed Dec. 19, 2016, which is a continuation of U.S. patent application Ser. No. 14/717,349, filed May 20, 2015, which is a continuation of U.S. patent application Ser. No. 13/848,809, filed Mar. 22, 2013, now U.S. Pat. No. 9,072,760, issued on Jul. 7, 2015, which is a continuation of International Patent Application Serial No. PCT/US2011/053293, filed Sep. 26, 2011, which claims priority to U.S. Provisional Application Ser. No. 61/387,335, filed Sep. 28, 2010, and to U.S. Provisional Application Ser. No. 61/386,345, filed Sep. 24, 2010. The contents of each of the foregoing are incorporated by reference for all purposes as if fully set forth herein.

STATEMENT OF GOVERNMENTAL INTEREST

This invention was made with government support under GM078238 awarded by the National Institutes of Health and ST1429-14-01 awarded by the Department of Defense. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jun. 1, 2018, is named P14916-01_ST25.txt and is 2,875 bytes in size.

BACKGROUND OF THE INVENTION

The presence of endotoxins in the blood is called endotoxemia. It can lead to septic shock, if the immune response is severely pronounced. Moreover, endotoxemia of intestinal origin, especially, at the host-pathogen interface, is considered to be an important factor in the development of alcoholic hepatitis, which is likely to develop on the basis of the small bowel bacterial overgrowth syndrome and an increased intestinal permeability. It is also the source of neonatal necrotizing enterocolitis (NEC).

Lipopolysaccharides (LPS), including Lipid A may cause uncontrolled activation of mammalian immune systems with production of inflammatory mediators that may lead to septic shock. This inflammatory reaction is mediated by Toll-like receptor 4 (TLR4) which is responsible for immune system cell activation. Damage to the endothelial layer of blood vessels caused by these inflammatory mediators can lead to capillary leak syndrome, dilation of blood vessels and a decrease in cardiac function and can lead to septic shock. Pronounced complement activation can also be observed later in the course as the bacteria multiply in the blood. High bacterial proliferation triggering destructive endothelial damage can also lead to disseminated intravascular coagulation (DIC) with loss of function of certain internal organs such as the kidneys, adrenal glands and lungs due to compromised blood supply. The skin can show the effects of vascular damage often coupled with depletion of coagulation factors in the form of petechiae, purpura and ecchymoses. The limbs can also be affected, sometimes with devastating consequences such as the development of gangrene, requiring subsequent amputation. Loss of function of the adrenal glands can cause adrenal insufficiency and additional hemorrhage into the adrenals causes Waterhouse-Friderichsen syndrome, both of which can be life-threatening. It has also been reported that gonococcal LOS can cause damage to human fallopian tubes.

More specifically, NEC reflects the sudden inflammation and death of the infant's intestines, yet its causes remain obscure, and current therapy—which often includes surgery to remove the diseased intestine—still is associated with death in nearly half of patients. In seeking to identify the causes of NEC, the Hackam laboratory has identified that the premature infant intestine contains a TLR4 "switch", which is "turned on" in premature babies by bacteria, leading to NEC. Prior studies have shown that the administration of breast milk is protective, although this is unfortunately only available for a minority of patients. Using computer assisted drug design, Hackam and colleagues recently identified a novel molecule, whose analogues are found in breast milk, and which can safely "shut off" the TLR4 switch in mice and piglets, after oral administration. The current disclosure examines the role of a new set of analogs for the prevention or treatment of NEC using a well validated mouse model.

SUMMARY OF THE INVENTION

In accordance with an embodiment, the present invention provides a compound having the following formula:

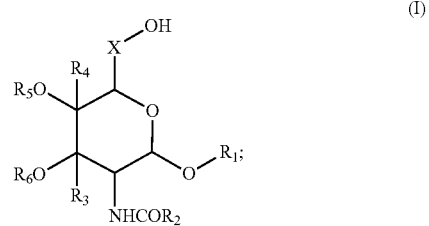

(I)

wherein $R_1$ is a $C_3$-$C_6$ branched or cyclic alkane, $R_2$ is H, or $C_1$-$C_4$ alkyl, $R_3$, $R_4$, $R_5$ and $R_6$ are each individually H, acyl, and $C_2$-$C_6$ alkyl or branched alkyl, X is $C_1$-$C_3$ alkyl, or a salt, solvate or stereoisomer thereof.

In accordance with an embodiment, the present invention provides a compound of formula I, having the following formula:

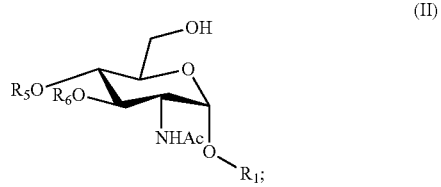

(II)

wherein $R_2$ is methyl, $R_3$ and $R_4$ are H, $R_5$ and $R_6$ are each individually H, and $C_2$-$C_6$ alkyl, and $R_1$ is a $C_3$-$C_6$ branched or cyclic alkane, or a salt, solvate or stereoisomer thereof, with the proviso that $R_5$ and $R_6$ cannot both be H or acyl and $R_1$ cannot be isopropyl.

In accordance with an embodiment, the present invention provides a compound having the following formula:

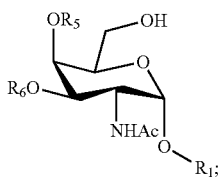
(III)

wherein $R_2$ is methyl, $R_3$ and $R_4$ are H, $R_5$ and $R_6$ are each individually H, and $C_2$-$C_6$ alkyl, and $R_1$ is a $C_3$-$C_6$ branched or cyclic alkane, or a salt, solvate or stereoisomer thereof, with the proviso that $R_5$ and $R_6$ cannot both be H or acyl and $R_1$ cannot be isopropyl.

In accordance with an embodiment, the present invention provides a compound of formula II having the formula:

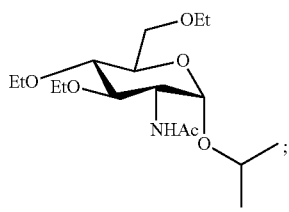
(C34-HP403)

or a salt, solvate or stereoisomer thereof.

In accordance with an embodiment, the present invention provides a compound of formula III having the formula:

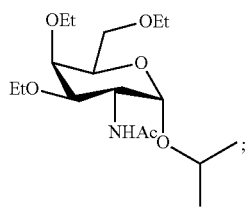

or a salt, solvate or stereoisomer thereof.

In accordance with an embodiment, the present invention provides a pharmaceutical composition comprising a therapeutically effective amount of a compound of formula (II):

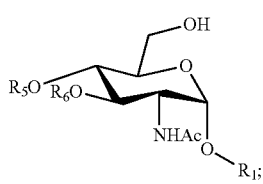
(I)

wherein $R_2$ is methyl, $R_3$ and $R_4$ are H, $R_5$ and $R_6$ are each individually H, and $C_2$-$C_6$ alkyl, and $R_1$ is a $C_3$-$C_6$ branched or cyclic alkane, or a salt, solvate or stereoisomer thereof, with the proviso that $R_5$ and $R_6$ cannot both be H or acyl and $R_1$ cannot be isopropyl, and a pharmaceutically acceptable carrier.

In accordance with an embodiment, the present invention provides a pharmaceutical composition comprising a therapeutically effective amount of a compound of formula (III):

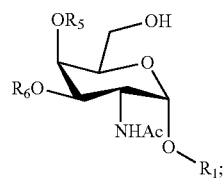
(III)

wherein $R_2$ is methyl, $R_3$ and $R_4$ are H, $R_5$ and $R_6$ are each individually H, and $C_2$-$C_6$ alkyl, and $R_1$ is a $C_3$-$C_6$ branched or cyclic alkane, or a salt, solvate or stereoisomer thereof, with the proviso that $R_5$ and $R_6$ cannot both be H or acyl and $R_1$ cannot be isopropyl, and a pharmaceutically acceptable carrier.

In accordance with an embodiment, the present invention provides a pharmaceutical composition comprising a therapeutically effective amount of a compound of formula (II) having the formula:

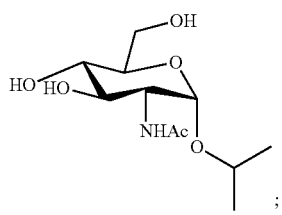
(C34 Triol)

or a salt, solvate or stereoisomer thereof, further comprising an effective amount of at least one additional biologically active agent.

In accordance with an embodiment, the present invention provides a pharmaceutical composition comprising a therapeutically effective amount of a compound of formula (III) having the formula:

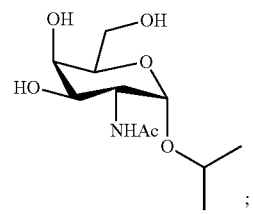

or a salt, solvate or stereoisomer thereof, further comprising an effective amount of at least one additional biologically active agent.

In accordance with another embodiment, the present invention provides a pharmaceutical compositions described above, further comprising an effective amount of at least one additional biologically active agent.

In accordance with a further embodiment, the present invention provides a method for treating an infectious or inflammatory disorder in a subject in need thereof comprising administering to the subject an effective amount of one or more compounds as described above.

In accordance with a further embodiment, the present invention provides a method for treating an intestinal inflammatory disorder in a subject in need thereof comprising administering to the subject an effective amount of one or more compounds as described above.

In accordance with a further embodiment, the present invention provides a method for treating a cardiovascular inflammatory disorder in a subject in need thereof comprising administering to the subject an effective amount of one or more compounds as described above.

In accordance with a further embodiment, the present invention provides a method for treating a pulmonary inflammatory disorder in a subject in need thereof comprising administering to the subject an effective amount of one or more compounds as described above.

In accordance with a further embodiment, the present invention provides a method for treating a traumatic injury in a subject in need thereof comprising administering to the subject an effective amount of one or more compounds as described above.

DETAILED DESCRIPTION OF THE INVENTION

Figure 1:
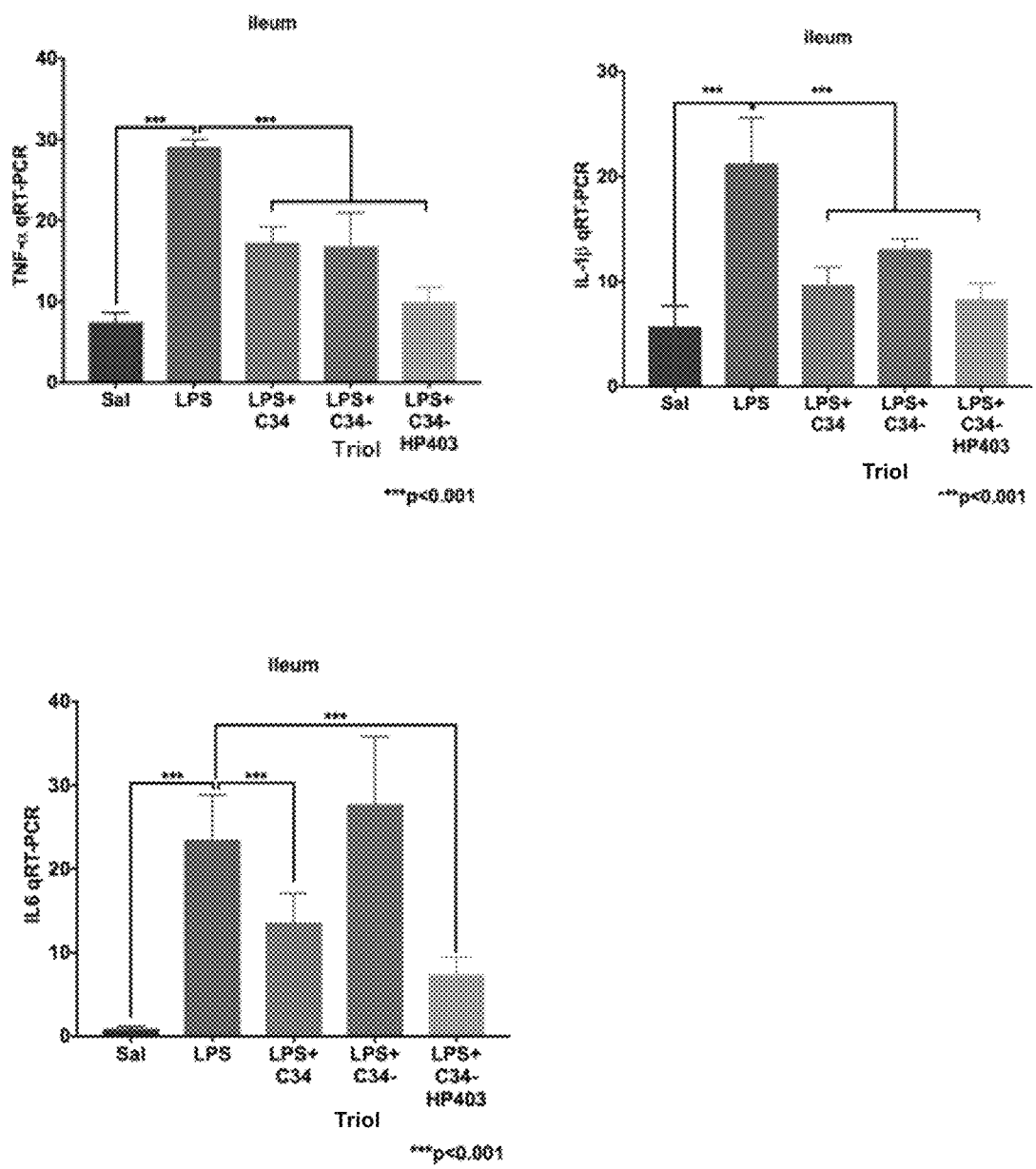
FIG. 1 illustrates the efficacy of C34, C34triol and C34-HP403 in endotoxemic model of mice. C57BL/6 mice ~3 weeks old were intraperitoneally injected with Sal (Saline/DMSO), LPS 10 mg/kg alone or co-injected with 10 mg/kg either C34, or C34-Trios, or C34-HP403. All mice were sacrificed 6 hrs later, small intestine (terminal ileum) was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 housekeeping genes was used to normalize gene expression and relative mRNA expression data was calculated using the 2-$\Delta\Delta$CT method.

In accordance with an embodiment, the present invention provides a compound having the following formula:

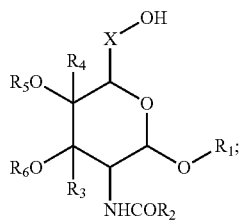

(I)

wherein $R_1$ is a $C_3$-$C_6$ branched or cyclic alkane, $R_2$ is H, or $C_1$-$C_4$ alkyl, $R_3$, $R_4$, $R_5$ and $R_6$ are each individually H, acyl, and $C_2$-$C_6$ alkyl, X is $C_1$-$C_3$ alkyl, or a salt, solvate or stereoisomer thereof.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise cycloalkyls have from about 3 to about 10 carbon atoms in their ring structure, and alternatively about 5, 6 or 7 carbons in the ring structure. As used herein, the compositions comprise hexosamines which are modified with short chain alkyl groups. Preferably alkyl groups between 2 to 6 carbons which may, or may not be substituted.

Moreover, the term "alkyl" (or "lower alkyl") includes both "unsubstituted alkyls" and "substituted alkyls," the latter of which refers to alkyl moieties having substituents replacing hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN and the like.

The terms "amine" and "amino" are art-recognized and include both unsubstituted and substituted amines. A primary amine carries two hydrogens, a secondary amine, one hydrogen and another substituent and a tertiary amine, the two hydrogens are substituted. The substituents for one or both of the hydrogens can be, for example, and alkyl, an alkenyl, and aryl, a cycloalkyl, a cycloalkenyl, a heterocycle, a polycycle and so on. If both hydrogens are substituted with carbonyls, the carbonyl framed nitrogen forms an imide.

The term "alkylamine" includes an amine group, as defined above, having a substituted or unsubstituted alkyl attached thereto.

The term "aryl" is art-recognized, and includes 5-, 6-, and 7-membered single ring aromatic groups that may include from zero to four heteroatoms, for example, benzene, pyrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydyl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls, and/or heterocyclyls, or rings joined by non-cyclic moieties.

The terms "ortho," "meta" and "para" are art-recognized and apply to 1,2-, 1,3- and 1,4-disubstituted cyclohexanes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocycclyl groups include, for example, thiophene, thianthrene, furan, pyran, isobenzofuran, chromene, xanthene, phenoxanthin, pyrrole imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphtyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones and the like. The heterocyclic ring may be substituted at one or more positions with such substituents as described above, as for example, halogen, alkyl aralkyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CD3, —CN or the like.

The terms "polycyclyl" and polycyclic group" are art-recognized and include structures with two or more rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hyroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CD3, —CN or the like.

The term "carbocycle" is art recognized and includes an aromatic or nonaromatic ring in which each atom of the ring is carbon. The following art-recognized terms have the following meanings: "nitro" means —NO$_2$; the term "halogen" designates —F, —Cl, —Br, or —I; the term "sulfhydryl" means —SH; the term "hydroxyl" or "hydroxy" means —OH; and the term sulfonyl" means —SO$_2$—.

The terms "amine" and "amino" are art-recognized and include both unsubstituted and substituted amines. A primary amine carries two hydrogens, a secondary amine, one hydrogen and another substituent and a tertiary amine, the two hydrogens are substituted. The substituents for one or both of the hydrogens can be, for example, and alkyl, an alkenyl, and aryl, a cycloalkyl, a cycloalkenyl, a heterocycle, a polycycle and so on. If both hydrogens are substituted with carbonyls, the carbonyl framed nitrogen forms an imide.

The term "alkylamine" includes an amine group, as defined above, having a substituted or unsubstituted alkyl attached thereto.

The term "amido" is art-recognized as an amino-substituted carbonyl.

The term "alkylthio" is art-recognized and includes and alkyl group, as defined above, having a sulfur radical attached thereto. In certain embodiments, the "alkylthio" moiety is represented by one of —S-alkyl, —S-alkenyl, —S-alkynyl and so on. Representative alkylthio groups include methylthio, ethylthio and the like.

The term "carbonyl" is art-recognized and includes a C=O structure. Carbonyls are involved in esters; carboxyl groups; formates; thiocarbonyls; thioesters; thiocarboxylic acids; thioformates; ketones; and aldehydes.

The terms "alkoxyl" and "alkoxy" are art-recognized and include an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl and so on.

The term "sulfonate" is art-recognized and includes a moiety wherein a sulfur atom carries two double bonded oxygens and a single bonded oxygen.

The term "sulfate" is art-recognized and includes a moiety that resembles a sulfonate but includes two single bonded oxygens.

The terms "sulfonamide," "sulfamoyl," "sulfonyl," and "sulfoxido" are art-recognized and each can include a variety of R group substituents as described herein.

The terms phosphoramidite" and "phophonamidite" are art-recognized.

The term "selenoalkyl" is art-recognized and includes an alkyl group having a substituted seleno group attached thereto. Exemplary "selenoethers" which may be substituted on the alkyl are selected from one of —Se-alkyl, —Se-alkenyl, —Se-alkynyl and so on.

Substitutions may be made to alkenyl and alkynyl groups to produce, for example, aminoalkenyls, aminoalkynyls, amidoalkenyls, iminoalkenyls, iminoalkynyls, thioalkenyls, thioalkynyls, carbonyl-substituted alkenyls or alkynyls.

It will be understood that "substitution" or "substituted with" includes the implicit proviso that such substitution is in accordance with the permitted valency of the substituted atom and the substituent, and that the substitution results in a stable compound, e.g., which does not spontaneously undergo transformation, such as by rearrangement, cyclization, elimination, or other reaction.

The term "substituted" is also contemplated to include all permissible substituents of organic compounds such as the imide reagent of interest. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

In accordance with an embodiment, the present invention provides a compound of formula I, having the following formula:

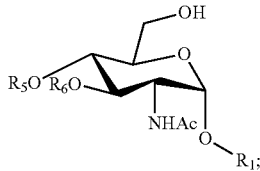

(II)

wherein $R_2$ is methyl, $R_3$ and $R_4$ are H, $R_5$ and $R_6$ are each individually H, and $C_2$-$C_6$ alkyl, and $R_1$ is a $C_3$-$C_6$ branched or cyclic alkane, or a salt, solvate or stereoisomer thereof, with the proviso that $R_5$ and $R_6$ cannot both be H or acyl and $R_1$ cannot be isopropyl.

In accordance with an embodiment, the present invention provides a compound having the following formula:

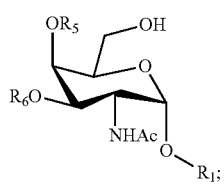

(III)

wherein $R_2$ is methyl, $R_3$ and $R_4$ are H, $R_5$ and $R_6$ are each individually H, and $C_2$-$C_6$ alkyl, and $R_1$ is a $C_3$-$C_6$ branched or cyclic alkane, or a salt, solvate or stereoisomer thereof, with the proviso that $R_5$ and $R_6$ cannot both be H or acyl and $R_1$ cannot be isopropyl.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

In accordance with an embodiment, the present invention provides a compound of formula II having the formula:

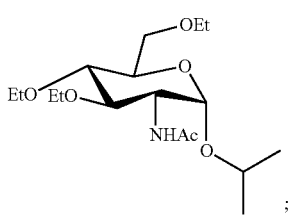

(C34-HP403)

or a salt, solvate or stereoisomer thereof.

In accordance with an embodiment, the present invention provides a compound of formula III having the formula:

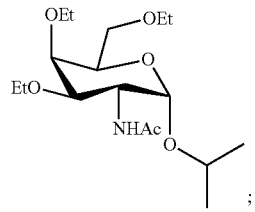

or a salt, solvate or stereoisomer thereof.

In accordance with an embodiment, the present invention provides a pharmaceutical composition comprising a therapeutically effective amount of a compound of formula (II):

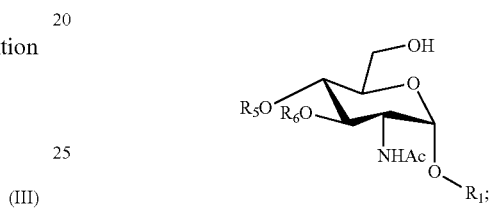

(I)

wherein $R_2$ is methyl, $R_3$ and $R_4$ are H, $R_5$ and $R_6$ are each individually H, and $C_2$-$C_6$ alkyl, and $R_1$ is a $C_3$-$C_6$ branched or cyclic alkane, or a salt, solvate or stereoisomer thereof, with the proviso that $R_5$ and $R_6$ cannot both be H or acyl and $R_1$ cannot be isopropyl, and a pharmaceutically acceptable carrier.

In accordance with an embodiment, the present invention provides a pharmaceutical composition comprising a therapeutically effective amount of a compound of formula (III):

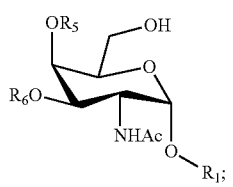

(III)

wherein $R_2$ is methyl, $R_3$ and $R_4$ are H, $R_5$ and $R_6$ are each individually H, and $C_2$-$C_6$ alkyl, and $R_1$ is a $C_3$-$C_6$ branched or cyclic alkane, or a salt, solvate or stereoisomer thereof, with the proviso that $R_5$ and $R_6$ cannot both be H or acyl and $R_1$ cannot be isopropyl, and a pharmaceutically acceptable carrier.

In some embodiments, the compounds and their use in the methods of the present invention are selected from the group consisting of:

1) 2-(acetylamino)-4-O-{2-(acetylamino)-4-O-[2-(acetylamino)-2-deoxy-beta-D-glucopyranosyl]-2-deoxy-beta-D-glucopyranosyl}-2-deoxy-D-glucopyranose;

2) N-{(1S,2S,3R)-1-[(beta-L-glycero-hexopyranosyloxy)methyl]-2,3-dihydroxyheptadecyl}hexacosanamide;

3) 4-O-(3-O-{2-(acetylamino)-2-deoxy-4-O-(6-deoxy-hexopyranosyl)-3-O-[2-O-(6-deoxyhexopyranosyl)hexopyranosyl]hexopyranosyl}hexopyranosyl)hexopyranose;

4) 3-acetamido-4,5-dihydroxy-6-(hydroxymethyl)tetrahydro-2H-pyran-2-yl dihydrogen phosphate, sodium salt;

5) 5-acetamido-6-((1R,2R)-3-(3-(3-acetamido-5-hydroxy-6-(hydroxymethyl)-4-(3,4,5-trihydroxy-6-(hydroxymethyl)tetrahydro-2H-pyran-2-yloxy)tetrahydro-2H-pyran-2-yloxy)-6-(4,5-dihydroxy-6-((E)-3-hydroxy-2-stearamidooctadec-4-e;

6) 3-O-(3-O-{2-(acetylamino)-2-deoxy-3-O-[2-O-(6-deoxyhexopyranosyl)hexopyranosyl]hexopyranosyl}hexopyranosyl)-D-arabinose;

7) cyclohexane-1,2,3,4,5,6-hexaylhexakis(dihydrogen phosphate), magnesium potassium salt;

8) cyclohexanamine compound with 1,6-di-O-phosphono-beta-D-glycero-hexopyranose (4:1) hydrate;

9) 1,2-O-(1-methylethylidene)-3-O-pentyl-6-O-[3,4,6-tri-O-acetyl-2-(acetylamino)-2-deoxy-beta-D-glucopyranosyl]-alpha-D-xylo-hexofuranose;

10) 6-O-[2-(acetylamino)-2-deoxy-beta-D-glucopyranosyl]-3-O-isopentyl-1,2-O-(1-methylethylidene)-alpha-D-xylo-hexofuranose;

11) (2S)-2-((4aR,6R,7R,8R,8aS)-7-acetamido-6-(2,3-bis(dodecyloxy)propoxy)-2,2-dimethylhexahydropyrano[3,2-d][1,3]dioxin-8-yloxy)propanoic acid;

12) propyl 3,4,6-tri-O-acetyl-2-(acetylamino)-2-deoxy-hexopyranoside;

13) octyl 2-(acetylamino)-2-deoxy-beta-D-glycero-hexopyranoside;

14) butyl 2-(acetylamino)-2-deoxy-3,4-di-O-methyl-beta-D-glucopyranoside;

15) sulfuric acid compound with (2R)-4-amino-N-{(1R,2S,3S,4R,5S)-5-amino-2-[(3-amino-3-deoxy-alpha-D-glucopyranosyl)oxy]-4-[(6-amino-6-deoxy-alpha-D-glucopyranosyl)oxy]-3-hydroxycyclohexyl}-2-hydroxybutanamide (1:1);

16) 2-(acetylamino)-2-deoxy-D-galactopyranose hydrate;

17) 1,2-O-(1-methylethylidene)-3-O-propyl-6-O-[3,4,6-tri-O-acetyl-2-(acetylamino)-2-deoxy-beta-D-glucopyranosyl]-alpha-D-xylo-hexofuranose;

18) Uridine 5'-diphospho-N-acetylgalactosamine disodium salt; 19) 2S,4S,5R,6R)-5-acetamido-2-((2R,3S,4S,5R,6S)-3,5-dihydroxy-2-(hydroxymethyl)-6-((2R,3S,4R,5S)-4,5,6-trihydroxy-2-(hydroxymethyl)tetrahydro-2*H*-pyran-3-yloxy);

20) methyl 2-(acetylamino)-2-deoxy-3-O-hexopyranosyl-hexopyranoside;

21) N-((2R,3R,4R,5S,6R)-4,5-dihydroxy-6-(hydroxymethyl)-2-(((3aR,5R,5aS,8aS,8bR)-2,2,7,7-tetramethyltetrahydro-3aH-bis[1,3]dioxolo[4,5-b:4',5'-d]pyran-5-yl)metho;

22) sec-butyl 2-(acetylamino)-2-deoxyhexopyranoside;

23) 2-(acetylamino)-2-deoxy-3-O-(6-deoxyhexopyranosyl)-4-O-hexopyranosylhexopyranose;

24) 1,3,4,6-tetra-O-acetyl-2-deoxy-2-(palmitoylamino)hexopyranose;

25) dimethyl 5-(acetylamino)-3,5-dideoxy-D-erythro-non-2-ulopyranosidonate;

26) octyl 2-(acetylamino)-2-deoxyhexopyranoside;

27) 2-(acetylamino)-2-deoxy-4-O-hexopyranosylhexopyranose;

28) [(4R)-5-acetamido-3,4,6-triacetyloxy-oxan-2-yl] methyl acetate;

29) (5-acetamido-3,4-diacetyloxy-6-pentoxy-oxan-2-yl) methyl acetate;

30) 2-((2R,5S)-3-acetamido-2,5-dihydroxy-6-(hydroxymethyl)tetrahydro-2H-pyran-4-yloxy)propanoic acid;

31) 2-(acetylamino)-2-deoxy-alpha-D-lyxo-hexopyranose;

32) sodium (2S,3S,4R,5R,6R)-3-((2S,3R,5S,6R)-3-acetamido-5-hydroxy-6-(hydroxymethyl)tetrahydro-2H-pyran-2-yloxy)-4,5,6-trihydroxytetrahydro-2H-pyran-2-carboxylate;

33) dodecyl 3,4,6-tri-O-acetyl-2-(acetylamino)-2-deoxy-beta-D-glucopyranoside;

34) isopropyl 3,4,6-tri-O-acetyl-2-(acetylamino)-2-deoxyhexopyranoside;

35) cyclohexyl 3,4,6-tri-O-acetyl-2-(acetylamino)-2-deoxy-alpha-D-glucopyranoside;

36) hexyl 3,4,6-tri-O-acetyl-2-(acetylamino)-2-deoxy-beta-D-glucopyranoside;

37) N-[(2R,3R,4R,5S,6R)-2-[(1'S,2'R,6R,8'R,9'S)-dispiro[cyclohexane-1,4'-[3,5,7,10,12]pentaoxatricyclo[7.3.0.0^{2,6}]dodecane-11',1''-cyclohexane]-8'-ylmethoxy]-4,5-dihydroxy-6-(hydroxymethyl)oxan-3-yl]acetamide;

38) (2R,3S,4R,5R,6R)-5-acetamido-2-(acetoxymethyl)-6-(((3aR,5R,5aS,8aS,8bR)-2,2,7,7-tetramethyltetrahydro-3a*H*-bis[1,3]dioxolo[4,5-b:4',5'-d]pyran-5-yl)methoxy)tetrahydr;

39) 6-O-[2-(acetylamino)-2-deoxy-beta-D-glucopyranosyl]-1,2-O-(1-methylethylidene)-3-O-propyl-alpha-D-xylo-hexofuranose;

40) (4R)-4-((S)-2-((2R)-2-((3R,4R,5S,6R)-3-acetamido-2,5-dihydroxy-6-(hydroxymethyl)tetrahydro-2H-pyran-4-yloxy)propanamido)propanamido)-5-amino-5-oxopentanoic acid;

41) Uridine 5'-diphospho-N-acetylglucosamine sodium salt;

42) 2-(acetylamino)-3-O-{4-O-[2-(acetylamino)-2-deoxy-3-O-alpha-D-xylo-hexopyranuronosyl-beta-D-ribo-hexopyranosyl]-beta-D-xylo-hexopyranuronosyl}-2-deoxy-D-glucopyranose;

43) 2-(acetylamino)-2-deoxy-3-O-(6,8-dideoxy-beta-L-glycero-octopyranosyl-7-ulose)-4-O-sulfo-L-erythro-hexopyranose;

44) 8-{[2-(acetylamino)-4-O-[2-(acetylamino)-2-deoxy-hexopyranosyl]-2-deoxy-6-O-(6-deoxyhexopyranosyl)hexopyranosyl]oxy}octyl acetate;

45) 2-(acetylamino)-2-deoxy-4-O-(6-deoxyhexopyranosyl)-3-O-hexopyranosylhexopyranose;

46) 2-(acetylamino)-2-deoxy-D-glucopyranose;

47) allyl 3,4,6-tri-O-acetyl-2-(acetylamino)-2-deoxy-beta-D-lyxo-hexopyranoside;

48) N-{(1S,2R,3E)-1-[(beta-L-ribo-hexopyranosyloxy)methyl]-2-hydroxy-3-heptadecenyl}octadecanamide;

49) sodium ((3S,6R)-5-acetamido-3,4,6-trihydroxytetrahydro-2H-pyran-2-yl)methyl phosphate;

50) allyl 2-(acetylamino)-2-deoxy-beta-D-glycero-hexopyranoside;

51) 1,3,4,6-tetra-O-acetyl-2-(acetylamino)-2-deoxy-beta-D-glycero-hexopyranose;

52) 2-(acetylamino)-2-deoxy-beta-D-glycero-hexopyranose;

53) 4-O-[2-(acetylamino)-2-deoxyhexopyranosyl]-1,5-anhydro-2-deoxyhexitol;

54) ethyl 2-(acetylamino)-2-deoxy-beta-D-glycero-hexopyranoside;

55) ethyl 3,4,6-tri-O-acetyl-2-(acetylamino)-2-deoxy-beta-D-glycero-hexopyranoside;

56) nonyl 2-(acetylamino)-2-deoxy-beta-D-glycero-hexopyranoside;

57) octadecyl 2-(acetylamino)-2-deoxy-beta-D-glycero-hexopyranoside;

58) 4-O-{6-O-[5-(acetylamino)-3,5-dideoxy-D-erythro-non-2-ulopyranonosyl]hexopyranosyl}hexopyranose;

59) 2-deoxy-2-(propionylamino)-D-glucopyranose;

60) 1,3,4,6-tetra-O-acetyl-2-(acetylamino)-2-deoxy-beta-D-glucopyranose;

61) [5-acetamido-3-acetyloxy-2-(acetyloxymethyl)-6-hexadecoxy-oxan-4-yl]acetate;

62) (5-acetamido-3,4-diacetyloxy-6-methoxy-oxan-2-yl) methyl acetate;

63) N-[2-ethoxy-4,5-dihydroxy-6-(hydroxymethyl)oxan-3-yl]acetamide;

64) [2,5-diacetyloxy-6-(acetyloxymethyl)-3-(dodecanoylamino)oxan-4-yl]acetate; and 65) N-[2-(dispiro[BLAH]ylmethoxy)-4,5-dihydroxy-6-(hydroxymethyl)oxan-3-yl]acetamide.

The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents.

As used herein, the term "surfactant" refers to organic substances having amphipathic structures, namely, are composed of groups of opposing solubility tendencies, typically an oil-soluble hydrocarbon chain and a water-soluble ionic group. Surfactants can be classified, depending on the charge of the surface-active moiety, into anionic, cationic and nonionic surfactants. Surfactants often are used as wetting, emulsifying, solubilizing and dispersing agents for various pharmaceutical compositions and preparations of biological materials.

Pharmaceutically acceptable salts are art-recognized, and include relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di-, or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenthylamine; (trihydroxymethyl) aminoethane; and the like, see, for example, J. Pharm. Sci., 66: 1-19 (1977).

In accordance with an embodiment, the present invention provides a pharmaceutical composition comprising a therapeutically effective amount of a compound of formula (II) having the formula:

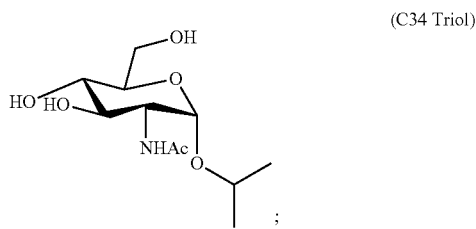

(C34 Triol)

or a salt, solvate or stereoisomer thereof, further comprising an effective amount of at least one additional biologically active agent.

In accordance with an embodiment, the present invention provides a pharmaceutical composition comprising a therapeutically effective amount of a compound of formula (III) having the formula:

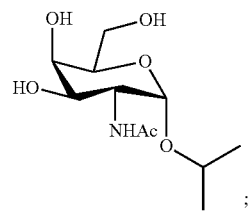

or a salt, solvate or stereoisomer thereof, further comprising an effective amount of at least one additional biologically active agent.

In accordance with another embodiment, the present invention provides a pharmaceutical compositions described above, further comprising an effective amount of at least one additional biologically active agent.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

Non-limiting examples of biologically active agents include following: anti-asthmatic agents, anti-allergenic materials, anti-inflammatory agents such as steroids, non-steroidal anti-inflammatory agents, anti-neoplastic agents, anti-pyretic and analgesic agents, antihistamines, benzophenanthridine alkaloids, biologicals, cardioactive agents, cerebral dilators, coronary dilators, decongestants, diuretics, diagnostic agents, gastrointestinal sedatives, agents, growth factors, peripheral vasodilators, and prodrugs. anti-infective agents, such as mupirocin; antianaerobic anti-infectives, such as chloramphenicol and clindamycin; antifungal antibiotic anti-infectives, such as amphotericin b, clotrimazole, fluconazole, and ketoconazole; macrolide antibiotic anti-infectives, such as azithromycin and erythromycin; miscellaneous antibiotic anti-infectives, such as and imipenem; penicillin, antibiotic anti-infectives, such as nafcillin, oxacillin, penicillin G, and penicillin V; quinolone antibiotic anti-infectives, such as ciprofloxacin and norfloxacin; tetracycline antibiotic anti-infectives, such as doxycycline, minocycline and tetracycline.

In accordance with a further embodiment, the present invention provides a method for treating an infectious or inflammatory disorder in a subject in need thereof comprising administering to the subject an effective amount of one or more inventive compounds as described above.

In some embodiments, the methods or use of the compounds for treating an infectious or inflammatory disorder in a subject in need thereof include the following compounds selected from the group consisting of:

In accordance with a further embodiment, the present invention provides a method for treating an intestinal inflammatory disorder in a subject in need thereof comprising administering to the subject an effective amount of one or more inventive compounds as described above.

In some embodiments, the methods or use of the compounds for treating an intestinal inflammatory disorder in a subject in need thereof include the following compounds selected from the group consisting of:

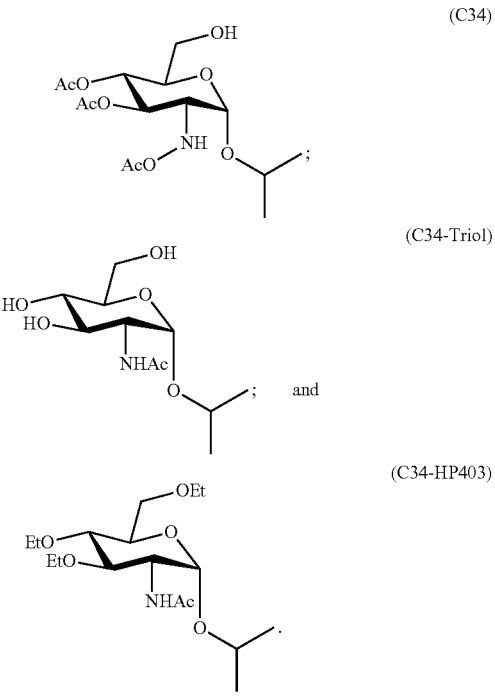

In accordance with a further embodiment, the present invention provides a method for treating a cardiovascular inflammatory disorder in a subject in need thereof comprising administering to the subject an effective amount of one or more compounds as described above.

In some embodiments, the methods or use of the compounds for treating a cardiovascular inflammatory disorder in a subject in need thereof include the following compounds selected from the group consisting of:

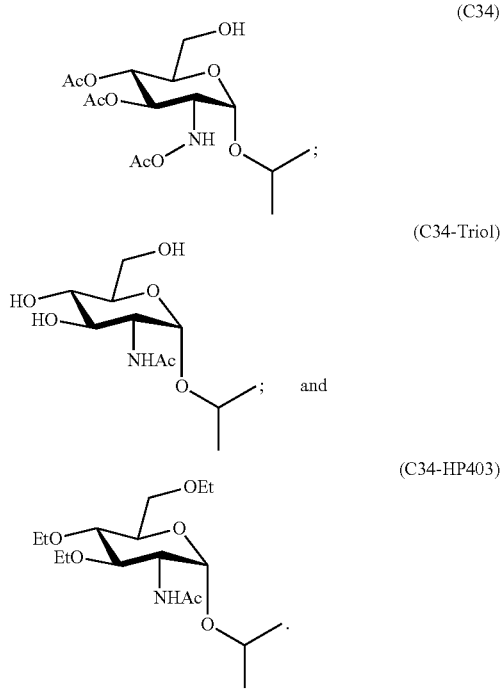

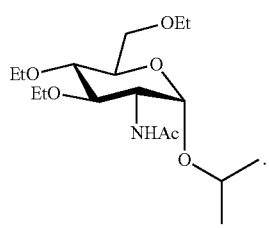
(C34-HP403)

In accordance with a further embodiment, the present invention provides a method for treating a pulmonary inflammatory disorder in a subject in need thereof comprising administering to the subject an effective amount of one or more compounds as described above.

In some embodiments, the methods or use of the compounds for treating a pulmonary inflammatory disorder in a subject in need thereof include the following compounds selected from the group consisting of:

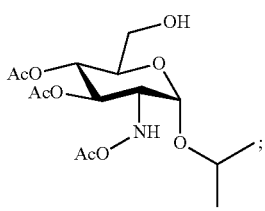
(C34)

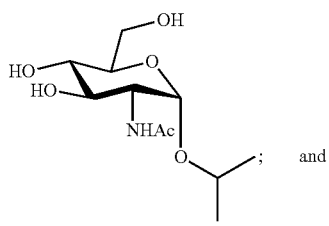
(C34-Triol) ; and

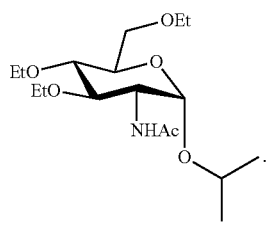
(C34-HP403)

In accordance with a further embodiment, the present invention provides a method for treating a traumatic injury in a subject in need thereof comprising administering to the subject an effective amount of one or more compounds as described above.

In some embodiments, the methods or use of the compounds for treating a traumatic injury in a subject in need thereof include the following compounds selected from the group consisting of:

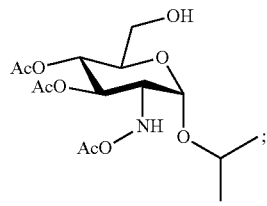
(C34)

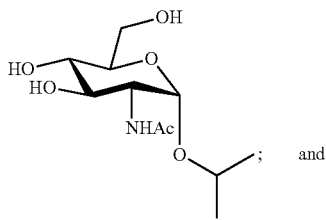
(C34-Triol) ; and

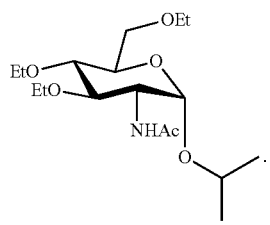
(C34-HP403)

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

LPS Induced Endotoxemia Model.

In general, C57BL/6 mice ~3 weeks old were intraperitoneally injected with Saline/DMSO, lipopolysaccharides (LPS) 5 mg/kg alone or co-injected with compounds (10 mg/kg). All mice were sacrificed 6 hours later and small intestine (terminal ileum) and lungs were harvested for RNA isolation and histology.

LPS Treatment in IEC6 Cells.

In general, intestinal epithelial (IEC6) cells were overnight plated in 12-well plates in 10% growth media without antibiotics and treated with DMSO (vehicle), LPS (25 µg/ml) alone or co-treated with compounds (10 mg/ml) for 6 hours. At the end of treatments, cells were harvested for total RNA isolation.

RNA isolation and measurements of pro-inflammatory cytokines by Quantitative Real-time Polymerase Reaction (qRT-PCR).

In general, total RNA was isolated from small intestine (ileum), lungs, and IEC6 cells using RNeasy® kit, checked for RNA purity, and concentration on SpectraMax® microplate reader. 0.5 µg of total RNA was reverse transcribed for cDNA synthesis using the QuantiTect® Reverse Transcription kit. qRT-PCR was then performed on a Bio-Rad CFX96 Real-Time System using Sybr green mix and gene specific primers as given table below. The mRNA expression relative to the housekeeping gene ribosomal protein large P0 (Rplp0) was calculated using the 2-ΔΔCT method. The primers used for qRT-PCR are shown in Table 1.

TABLE 1

Primers for qRT-PCR

| Gene | Forward sequence | Reverse sequence | Amplicon Size (bp) |
|---|---|---|---|
| Mouse IL-1β | AGTGTGGATCCCAAGCAAT ACCCA (SEQ ID NO: 1) | TGTCCTGACCACTGTTGTTTCCCA (SEQ ID NO: 2) | 175 |
| Rat iNOS | CTGCTGGTGGTGACAAGCAC ATTT (SEQ ID NO: 3) | ATGTCATGAGCAAAGGCGCAGA AC (SEQ ID NO: 4) | 167 |
| Mouse Lipocalin-2 | ACAACCAGTTCGCCATGGTA T (SEQ ID NO: 5) | AAGCGGGTGAAACGTTCCTT (SEQ ID NO: 6) | 121 |
| Mouse MPO | GACAGTGTCAGAGATGAAG CTACT (SEQ ID NO: 7) | TTGATGCTTTCTCTCCGCTCC (SEQ ID NO: 8) | 189 |
| Mouse PUMA | GCAGTACGAGCGGCGGAGA C (SEQ ID NO: 9) | GGGCGGGTGTAGGCACCTAGT (SEQ ID NO: 10) | 149 |
| Mouse TNF-α | TTCCGAATTCACTGGAGCCT CGAA (SEQ ID NO: 11) | TGCACCTCAGGGAAGAATCTGGA A (SEQ ID NO: 12) | 144 |
| Rat TNF-α | CATCTTCTCAAAATTCGAGT GACAA (SEQ ID NO: 13) | TGGGAGTAGACAAGGTACAACCC (SEQ ID NO: 14) | 175 |
| Rpl0 | GGCGACCTGGAAGTCCAAC T (SEQ ID NO: 15) | CCATCAGCACCACAGCCTTC (SEQ ID NO: 16) | 143 |

Histology Using Hematoxylin and Eosin (H&E) and Myeloperoxidase Staining

Generally, freshly harvested ileum and lung tissues were quickly fixed in 4% paraformaldehyde, processed for paraffin blocks, sectioned (5 μm), stained with Hematoxylin & Eosin (H&E) staining and imaged using EVOS imaging system. For immunostaining, paraffin sections were immunostained for inflammatory neutrophils (PMNs) using Myeloperoxidase antibody. Briefly, 5 μm paraffin sections were processed for citrate antigen retrieval, followed by overnight incubation with Myeloperoxidase primary antibody, washed and incubated with secondary antibody, and stained with DAB staining.

Exemplary Synthesis of C34-Triol.

The synthesis starts with C34 and uses a saponification to generate C34 triol. Protocol as follows: C-34 (0.425 g, 1.09 mmol) was added to a round bottom flask (50 mL) with a small stir bar. A stock solution 1.0 N sodium hydroxide was made up by dissolving 0.313 g of NaOH in 9.38 mL of water. The NaOH stock solution (6.42 mL) was added to the round bottom flask along with 16.4 mL of THF. The mixture was capped and stirred. The reaction was monitored via LCMS. After 160 minutes, LCMS indicated that full conversion had taken place. The reaction mixture was evaporated to almost dryness and aziotroped with toluene (8×3 mL) until a yellow-white solid had formed. A mass of the solid indicated approximately 800 mg of impure product. The impure product was put through a small column (4 in of Sift) eluting with chloroform:methanol (7:1) to separate the desired product from sodium acetate. The elutant was evaporated to give 0.212 g of desired product (73.8% yield). Purity was confirmed via HRMS and ELS and the separation of desired compound from sodium acetate was confirmed with proton NMR (CD$_3$OD). Related methods can be used to generate partially saponified analogs, and alcohols derived from other substitutions at the anomeric carbon and the C(2) carbon of the pyran ring. Also, this protocol can be used for various stereoisomers of C34 and related esters, which can be assessed in experimental models of endotoxemia and/or necrotizing enterocolitis.

Example 1

The efficacy of C34, C34-triol and C34-HP403 in endotoxemic model of mice.

C57BL/6 mice ~3 weeks old were intraperitoneally injected with Sal (Saline/DMSO), LPS 10 mg/kg alone or co-injected with 10 mg/kg either C34, or C34-Trios, or C34-HP403. All mice were sacrificed 6 hours later, small intestine (terminal ileum) was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 house keeping genes was used to normalize gene expression and relative mRNA expression data was calculated using the 2-ΔΔCT method (FIG. 1).

Example 2

Potency and efficacy comparison of C34, C34triol and C34-HP403 in intestinal epithelial cells challenged with LPS.

Figure 2:
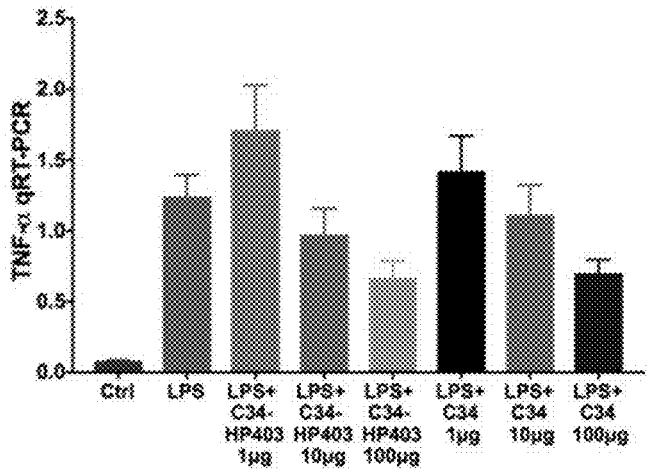
FIG. 2: Potency and efficacy comparison of C34, C34triol and C34-HP403 in intestinal epithelial cells challenged with LPS. C57BL/6 mice 3 weeks old were intraperitoneally injected with Sal (Saline/DMSO), LPS 10 mg/kg alone or co-injected with C34 or C34-HP403 at indicated dosages. All mice were sacrificed 6 hrs later, small intestine (terminal ileum) was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 housekeeping genes was used to normalize gene expression and relative mRNA expression data was calculated using the 2-$\Delta\Delta$CT method.
Figure 2:
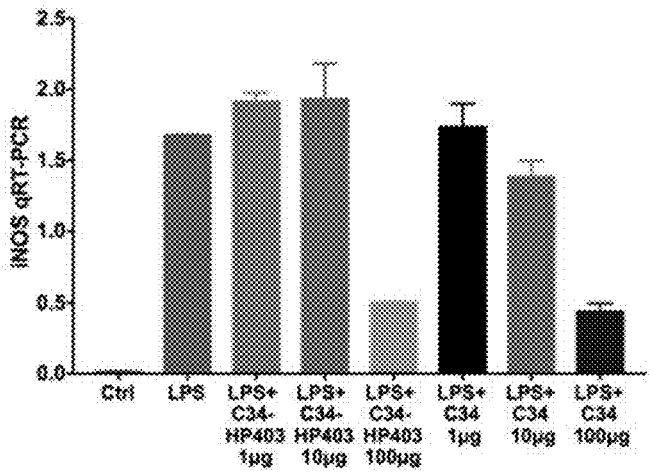
Figure 2:
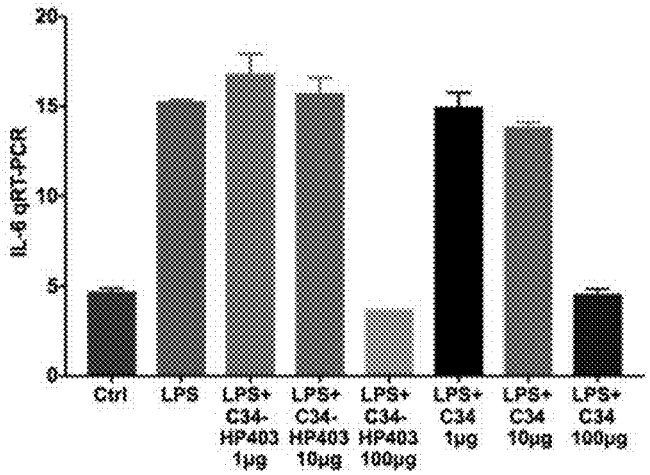

C57BL/6 mice 3 weeks old were intraperitoneally injected with Sal (Saline/DMSO), LPS 10 mg/kg alone or co-injected with C34 or C34-HP403 at indicated dosages (FIG. 2). All mice were sacrificed 6 hrs later, small intestine (terminal ileum) was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 house keeping genes was used to normalize gene expression and relative mRNA expression data was calculated using the 2-ΔΔCT method.

Example 3

Efficacy of C34-HP403 and LacNAc-heptaacetate in endotoxemic model of mouse.

Figure 3:
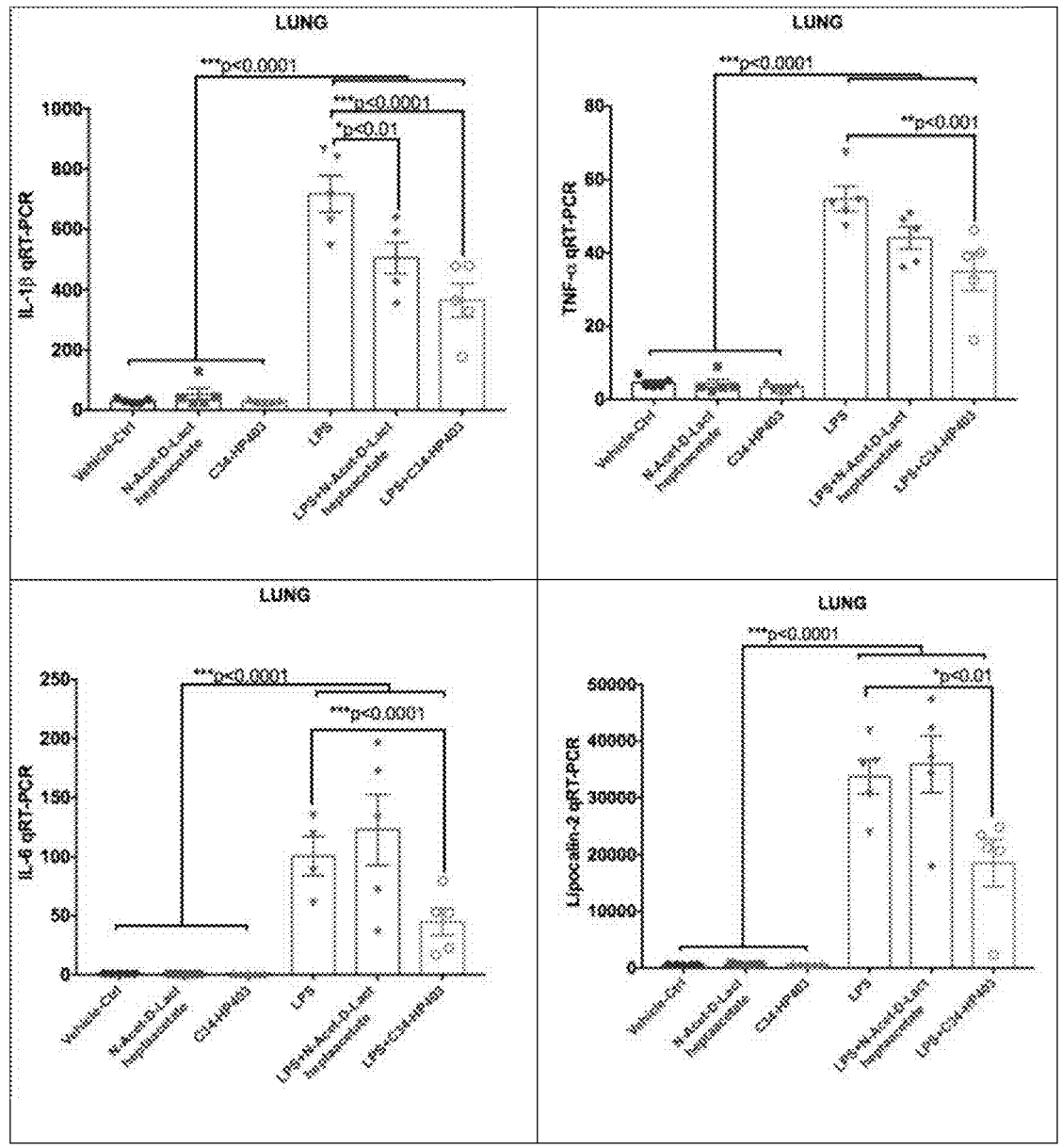
FIG. 3: Efficacy of C34-HP403 and LacNAc-heptaacetate in endotoxemic model of mouse. C57BL/6 mice 3 weeks old were intraperitoneally injected with Sal (Saline/DMSO), LPS 10 mg/kg, N-acetyl-D-Lactosamine heptaacetate (10 mg/kg), C34-HP403 (10 mg/kg) alone or co-injected with LPS. All mice were sacrificed 6 hrs later, lung tissue was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 housekeeping genes were used to normalize gene expression and relative mRNA expression data was calculated using the 2-$\Delta\Delta$CT method.

C57BL/6 mice 3 weeks old were intraperitoneally injected with Sal (Saline/DMSO), LPS 10 mg/kg, N-acetyl-D-Lactosamine heptaacetate (10 mg/kg), C34-HP403 (10 mg/kg) alone or co-injected with LPS (FIG. 3). All mice were sacrificed 6 hrs later, lung tissue was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 house keeping genes was used to normalize gene expression and relative mRNA expression data was calculated using the 2-ΔΔCT method.

Example 4

Comparison of C34 and C34-triol in IEC-6 cells treated with LPS.

Figure 4:
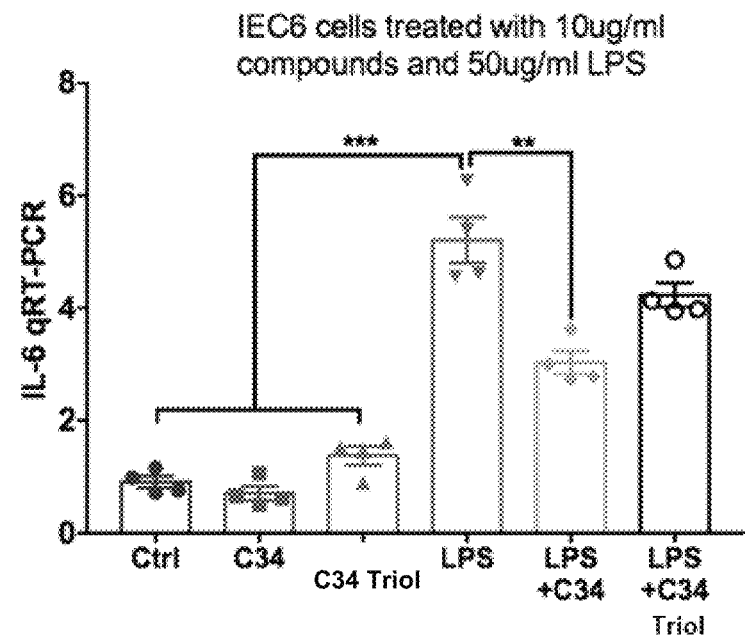
FIG. 4: Comparison of C34 and C34-triol in IEC-6 cells treated with LPS. Intestinal epithelial cells were plated overnight in 6-well plates with expected 70-80% confluency. Cells were treated Sal (Saline/DMSO), LPS 50 mg/ml, C34 (10 mg/ml), C34-Trios (10 mg/ml) alone in combination with LPS. Compounds were added 1 hr before addition of LPS as pretreatment (total treatment time is 7 hrs). Total RNA was isolated using Qiagnen RNeasy kit and reverse-transcribed into cDNA using Qiagen QuantiTect Reverse Transcription kit. mRNA expression of pro-inflammatory cytokines was amplified using gene-specific forward and reverse primers with BioRad iQ SYBR Green Supermix on CFX96 thermal cycler. Rplp0 housekeeping genes were used to normalize gene expression and relative expression data was calculated using the 2-$\Delta\Delta$CT method.
Figure 4:
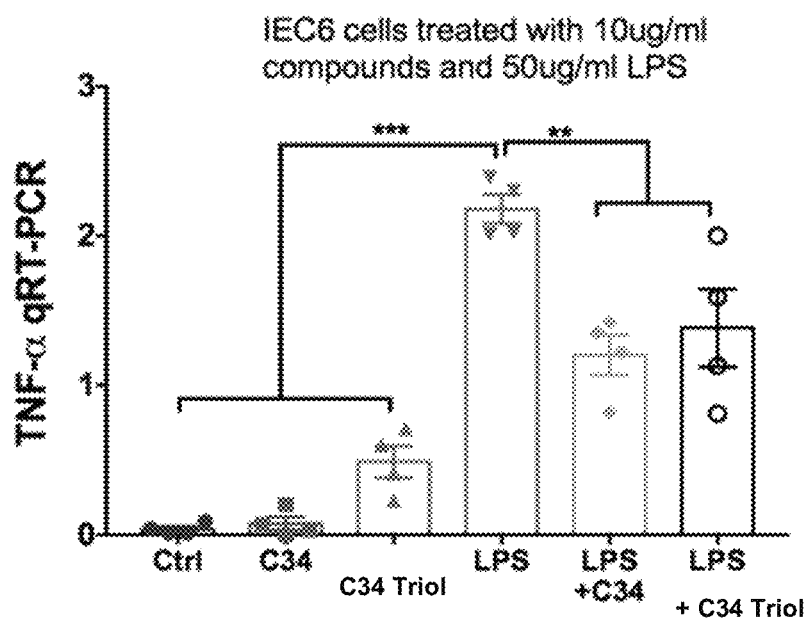
Figure 5:
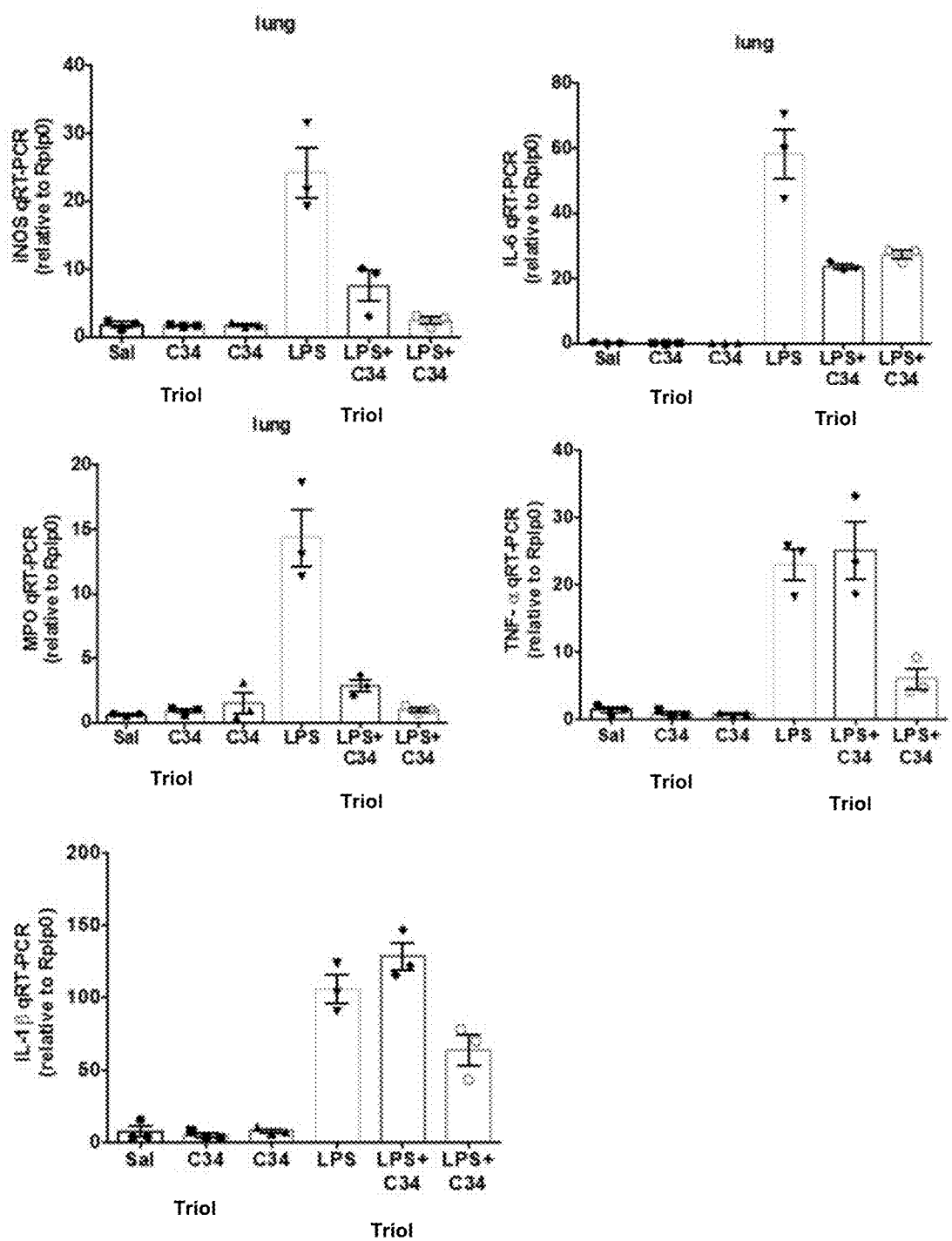
FIG. 5: Effect of C34, C34-triol and C34-HP403 on LPS exposure. C57BL/6 mice 3 weeks old were intraperitoneally injected with Sal (Saline/DMSO), LPS 10 mg/kg alone or co-injected with 10 mg/kg either of C34, or C34-triol, or C34-HP403. All mice were sacrificed 6 hrs later, lung tissue was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 housekeeping genes were used to normalize gene expression and relative mRNA expression data was calculated using the 2-$\Delta\Delta$CT method.
Figure 6:
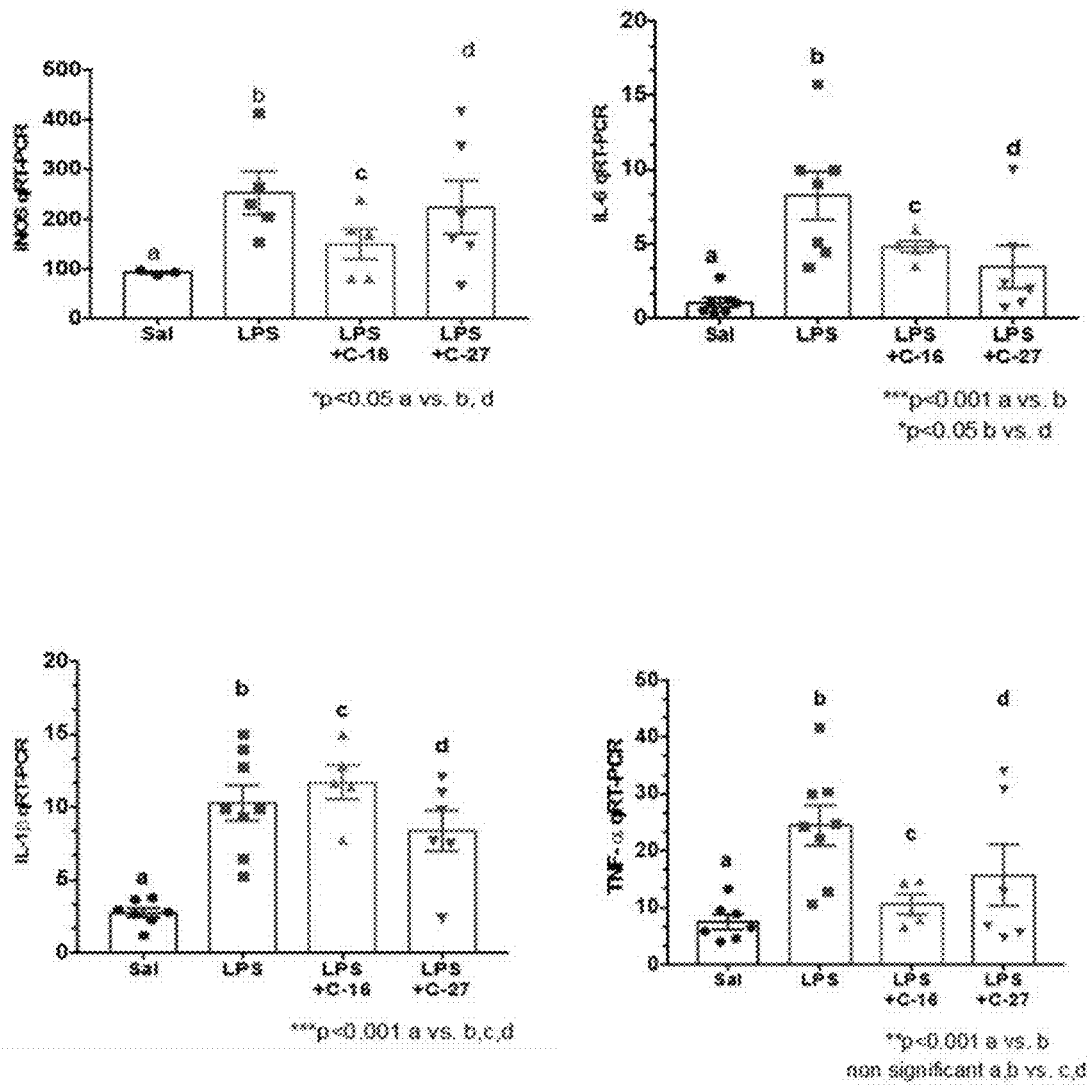
FIG. 6: Effect of LPS 5 mg/kg and co-injection of compounds C-16 (N-acetylgalactosamine) and C-27 (N-acetyl-lactosamine) at 10 mg/kg (i.p) for 6 hours in 3-weeks old C57BL/6 mice. C57BL/6 mice 3 weeks old were intraperitoneally injected with Sal (Saline/DMSO), LPS 10 mg/kg alone or co-injected with 10 mg/kg either of C16, or C27. All mice were sacrificed 6 hrs later, lung tissue was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 housekeeping genes were used to normalize gene expression and relative mRNA expression data was calculated using the 2-$\Delta\Delta$CT method.
Figure 6:
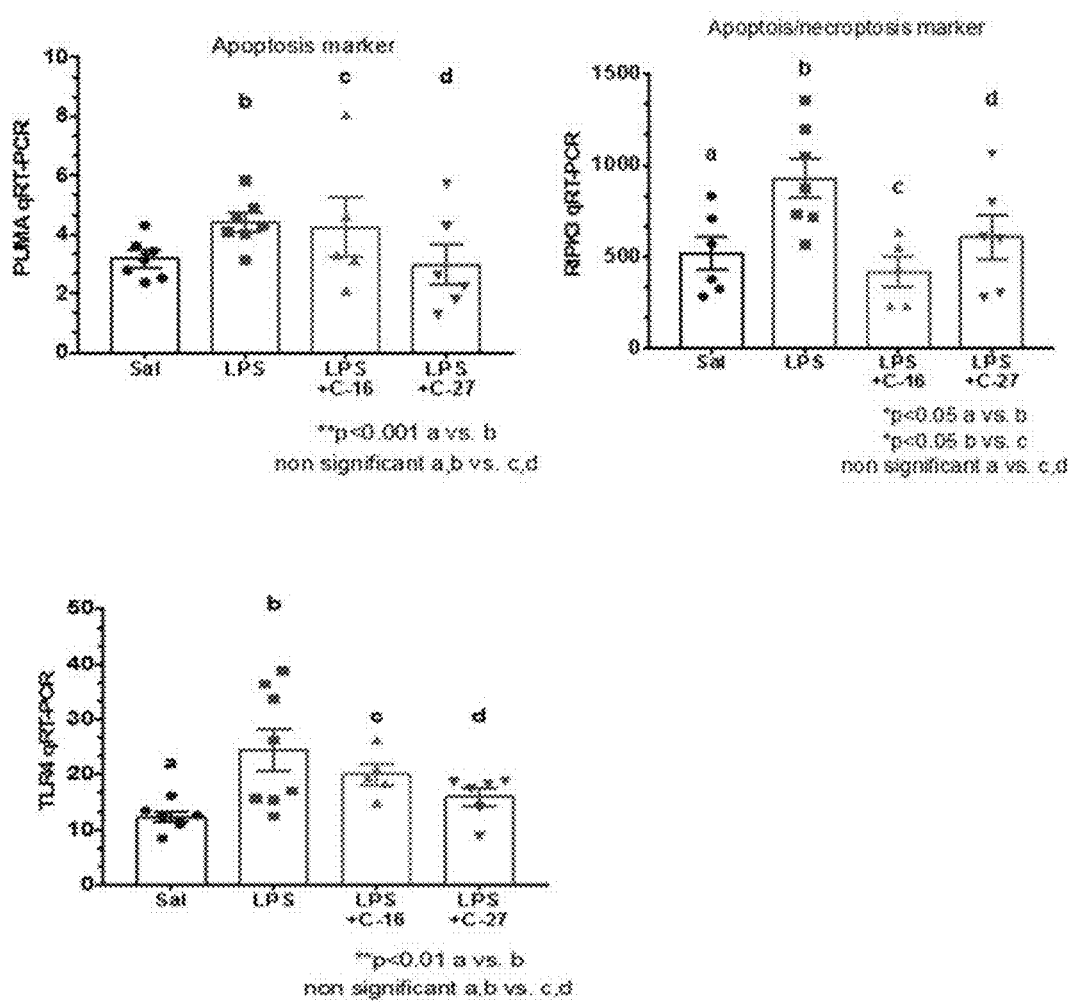
Figure 7:
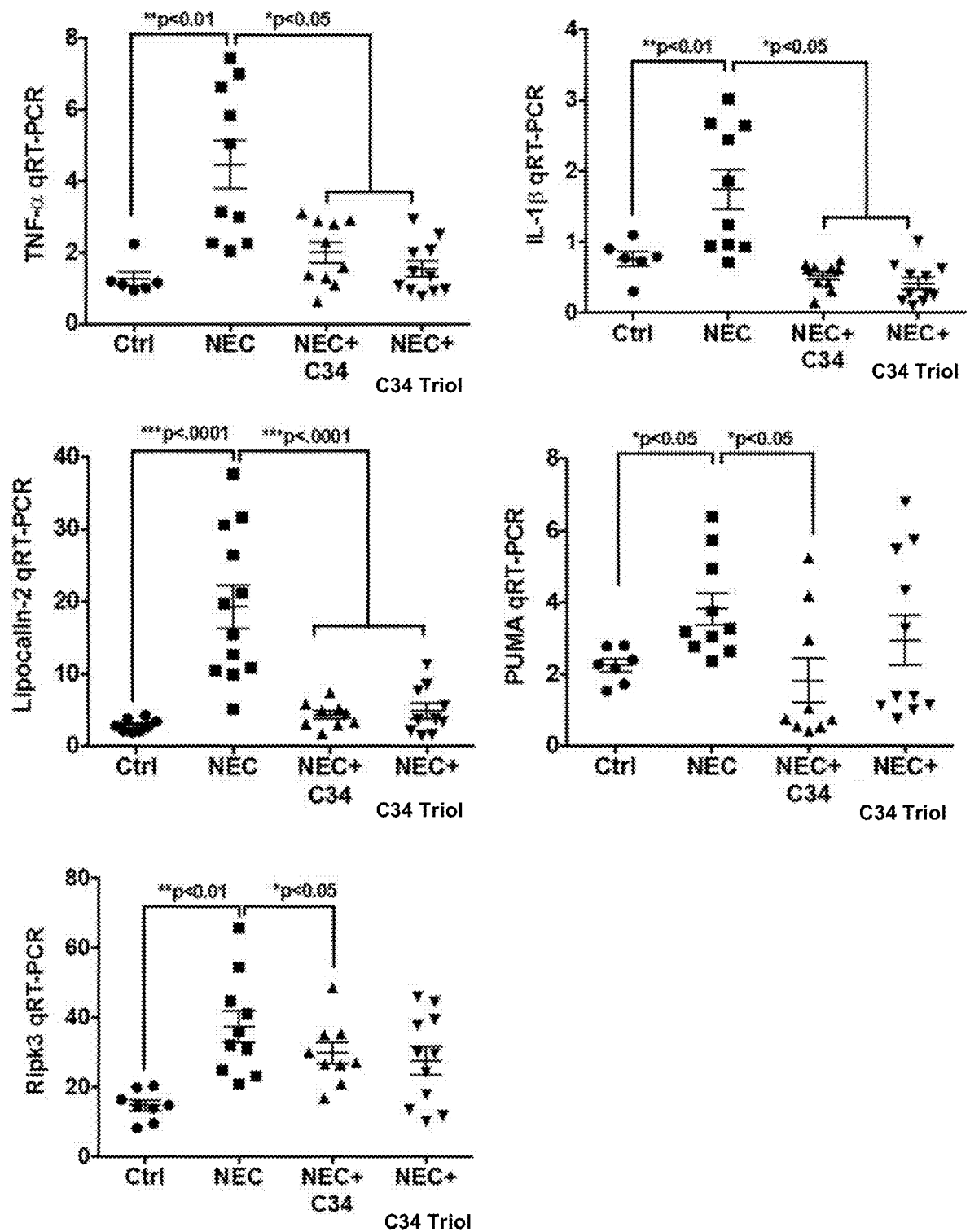
FIG. 7: NEC model C57/BL6 7-8 days old mice, subjected to NEC model with compounds mixed in NEC formula 10 mg/kg (2 mg/kg/feed or 10 mg/kg/day divided in 5 feeds). Control (Breast-fed) and NEC mice were sacrificed at same time on day 5 of treatments, small intestine (terminal ileum) was harvested for total RNA isolation using Qiagnen RNeasy kits, reverse-transcribed into cDNA using Qiagen QuantiTect Reverse Transcription kit. mRNA expression of pro-inflammatory cytokines and apototic/necroptosis genes were amplified using gene-specific forward and reverse primers with BioRad iQ SYBR Green Supermix on CFX96 thermal cycler. Rplp0 housekeeping genes was used to normalize gene expression and relative expression data was calculated using the 2-$\Delta\Delta$CT method.
Figure 8:
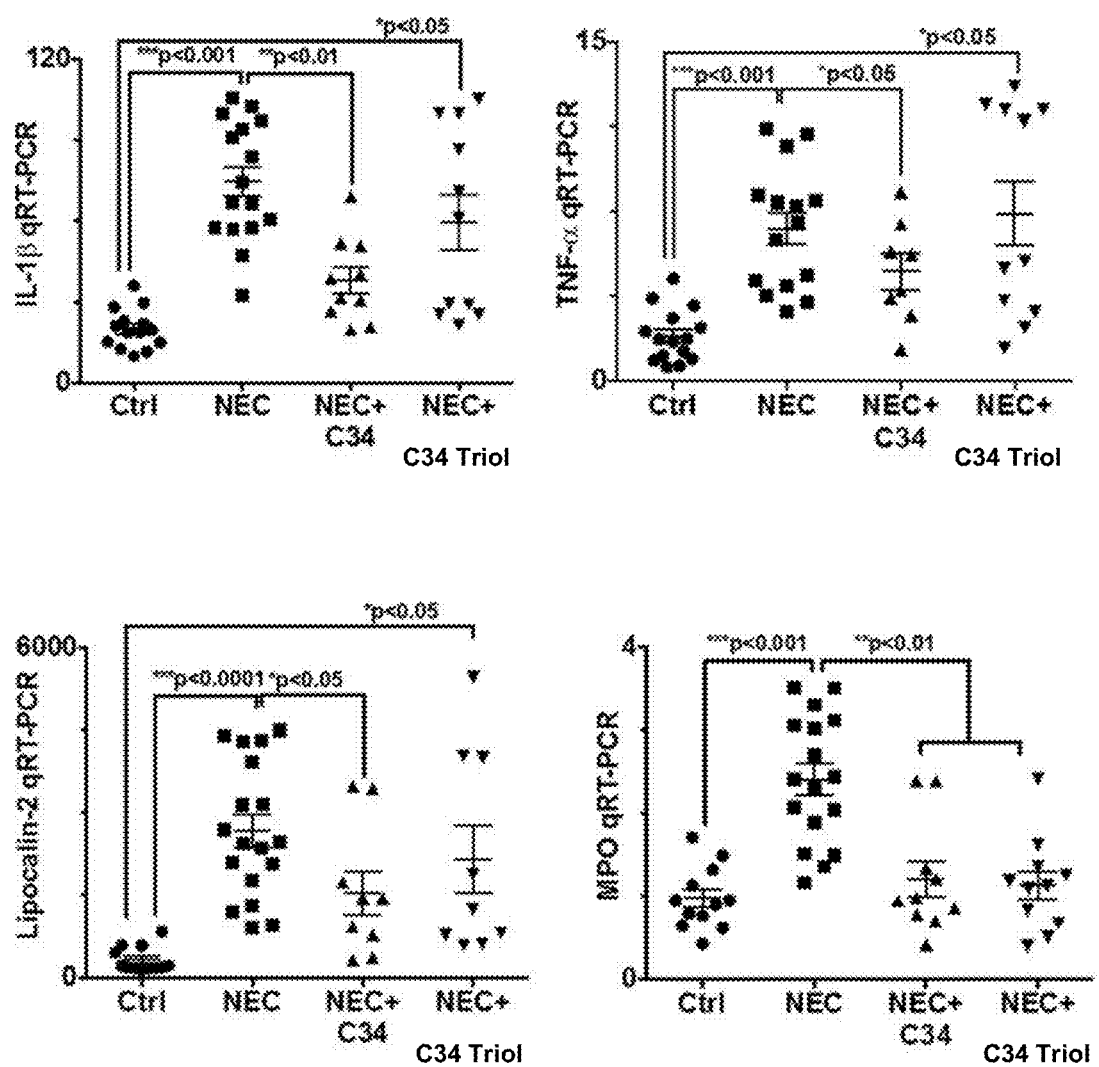
FIG. 8: NEC model C57/BL6 7-8 days old mice, subjected to NEC model with compounds mixed in NEC formula 10 mg/kg (2 mg/kg/feed or 10 mg/kg/day divided in 5 feeds). Control (Breast-fed) and NEC mice were sacrificed at same time on day 5 of treatments, lung tissue was harvested for total RNA isolation using Qiagnen RNeasy kits, reverse-transcribed into cDNA using Qiagen QuantiTect Reverse Transcription kit. mRNA expression of pro-inflammatory cytokines and apototic/necroptosis genes were amplified using gene-specific forward and reverse primers with BioRad iQ SYBR Green Supermix on CFX96 thermal cycler. Rplp0 housekeeping genes were used to normalize gene expression and relative expression data was calculated using the 2-ΔΔCT method.
Figure 9:
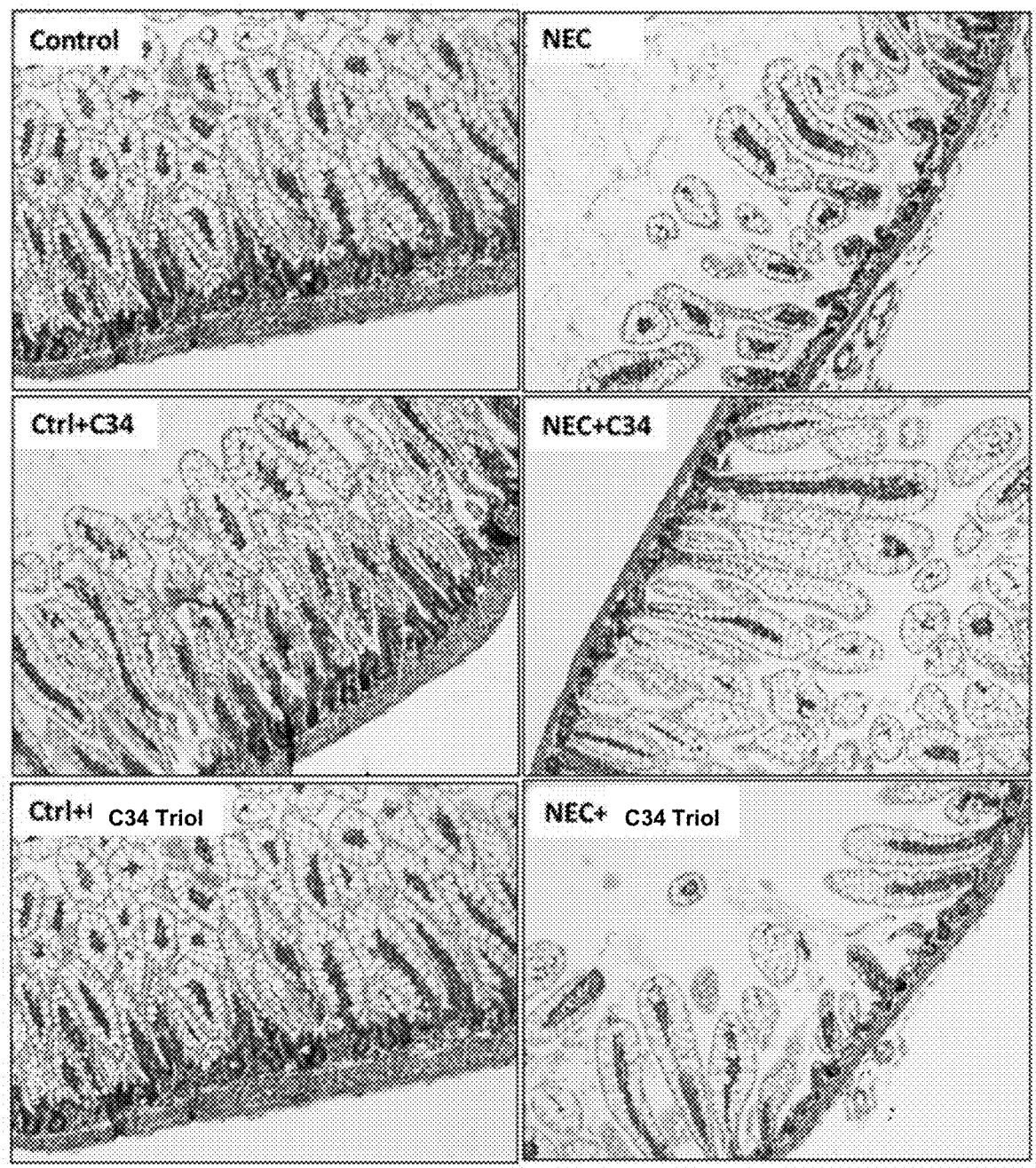
FIG. 9: C34 protects against NEC induced intestinal injury. C57/BL6 (7-8 days old) mice subjected to NEC inducing regimen and treated with compounds (10 mg/kg/day divided in 5 feeds) mixed in formula diet. Control (Breast milk-fed) and NEC mice were sacrificed on Day 5. Small intestine (terminal ileum) was fixed in 4% paraformaldehyde and paraffin blocks, sectioned (5 μm), stained with hematoxylin and eosin (H&E) and imaged with EVOS imaging system.
Figure 10:
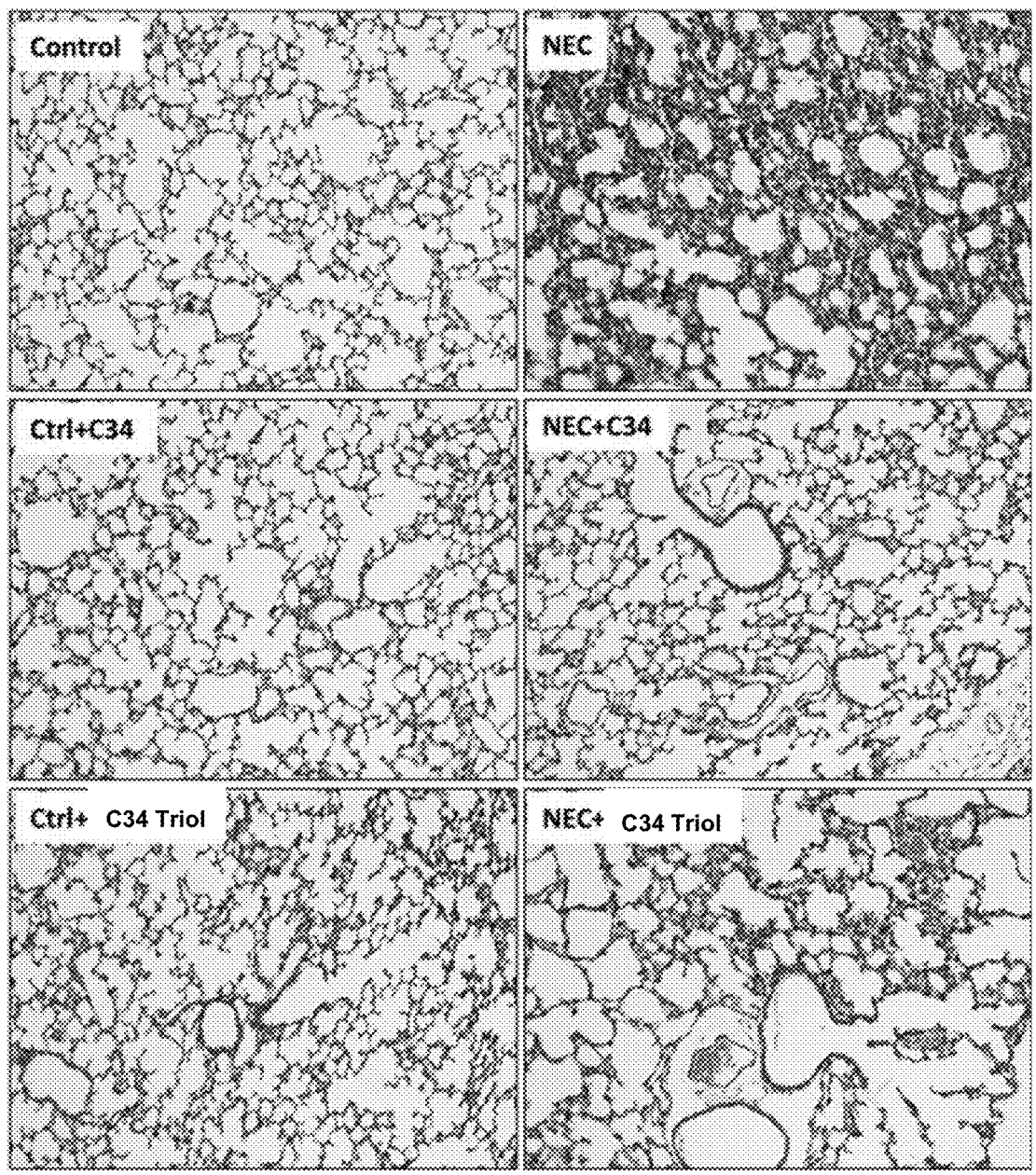
FIG. 10: C34 protects against NEC induced lung injury. C57/BL6 (7-8 days old) mice subjected to NEC inducing regimen and treated with compounds (10 mg/kg/day divided in 5 feeds) mixed in formula diet. Control (Breast milk-fed) and NEC mice were sacrificed on Day 5. Left lungs were fixed in 4% paraformaldehyde and paraffin blocks, sectioned (5 μm), stained with hematoxylin and eosin (H&E) and imaged with EVOS imaging system.
Figure 11:
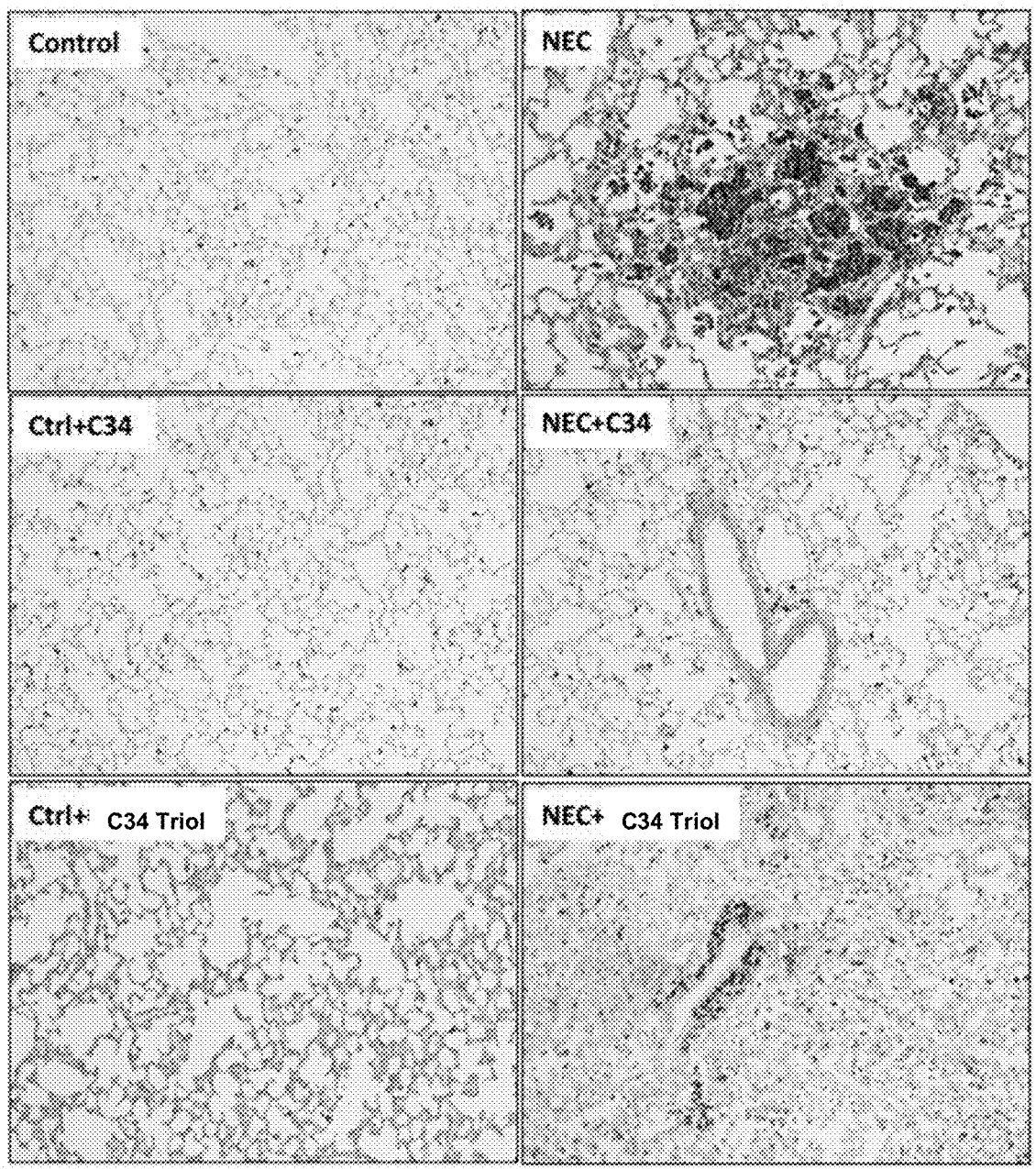
FIG. 11: C34 protects against NEC induced neutrophil infiltration in the lungs. C57/BL6 (7-8 days old) mice subjected to NEC inducing regimen and treated with compounds (10 mg/kg/day divided in 5 feeds) mixed in formula diet. Control (Breast milk-fed) and NEC mice were sacrificed on Day 5. Left lungs were fixed in 4% paraformaldehyde and paraffin blocks, sectioned (5 μm), stained for inflammatory neutrophils (PMNs) and imaged with EVOS imaging system.

Intestinal epithelial cells were plated overnight in 6-well plates with expected 70-80% confluency. Cells were treated Sal (Saline/DMSO), LPS 50 mg/ml, C34 (10 mg/ml), C34-Trios (10 mg/ml) alone in combination with LPS. Compounds were added 1 hr before addition of LPS as pretreatment (total treatment time is 7 hrs) (FIG. 4). Total RNA was isolated using Qiagnen RNeasy kit and reverse-transcribed into cDNA using Qiagen QuantiTect Reverse Transcription kit. mRNA expression of pro-inflammatory cytokines was amplified using gene-specific forward and reverse primers with BioRad iQ SYBR Green Supermix on CFX96 thermal cycler. Rplp0 house keeping genes was used to normalize gene expression and relative expression data was calculated using the 2-ΔΔCT method.

Example 5

Comparison of the effect of C34 and C34-triol in lung tissue of 3 week old mice exposed to LPS.

C57BL/6 mice 3 weeks old were intraperitoneally injected with Sal (Saline/DMSO), LPS 10 mg/kg alone or co-injected with 10 mg/kg either of C34, or C34-Triol, or C34-HP403. All mice were sacrificed 6 hrs later, lung tissue was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 house keeping genes was used to normalize gene expression and relative mRNA expression data was calculated using the 2-ΔΔCT method.

Example 6

Administration of LPS 5 mg/kg and co-injection of compounds C-16 (N-acetylgalactosamine) and C-27 (N-acetyllactosamine) 10 mg/kg (i.p) for 6 hours in 3-weeks old C57BL/6 mice.

C57BL/6 mice 3 weeks old were intraperitoneally injected with Sal (Saline/DMSO), LPS 10 mg/kg alone or co-injected with 10 mg/kg either of C16, or C27. All mice were sacrificed 6 hrs later, lung tissue was harvested for total RNA isolation using Qiagnen RNeasy kits and reverse-transcribed into cDNA using Qiagen QuantiTect Reverse Transcription kit. mRNA levels of pro-inflammatory cytokines was amplified using gene-specific forward and reverse primers with BioRad iQ SYBR Green supermix on CFX96 thermal cycler. Rplp0 house keeping genes was used to normalize gene expression and relative mRNA expression data was calculated using the 2-ΔΔCT method.

Example 7

Effect of compounds on intestinal inflammation of 8 day old mice in NEC model.

C57/BL6 7-8 day old mice, subjected to NEC model with compounds mixed in NEC formula 10 mg/kg (2 mg/kg/feed or 10 mg/kg/day divided in 5 feeds). Control (Breast-fed) and NEC mice were sacrificed at same time on day 5 of treatments, small intestine (terminal ileum) was harvested for total RNA isolation using Qiagnen RNeasy kits, reverse-transcribed into cDNA using Qiagen QuantiTect Reverse Transcription kit. mRNA expression of pro-inflammatory cytokines and apototic/necroptosis genes were amplified using gene-specific forward and reverse primers with BioRad iQ SYBR Green Supermix on CFX96 thermal cycler. Rplp0 house keeping genes was used to normalize gene expression and relative expression data was calculated using the 2-ΔΔCT method.

Example 8

Effect of compounds on lung inflammation of 8 day old mice in NEC model.

NEC model C57/BL6 7-8 day old mice, subjected to NEC model with compounds mixed in NEC formula 10 mg/kg (2 mg/kg/feed or 10 mg/kg/day divided in 5 feeds).

Control (Breast-fed) and NEC mice were sacrificed at same time on day 5 of treatments, lung tissue was harvested for total RNA isolation using Qiagnen RNeasy kits, reverse-transcribed into cDNA using Qiagen QuantiTect Reverse Transcription kit. mRNA expression of pro-inflammatory cytokines and apototic/necroptosis genes were amplified using gene-specific forward and reverse primers with BioRad iQ SYBR Green Supermix on CFX96 thermal cycler. Rplp0 housekeeping genes were used to normalize gene expression and relative expression data was calculated using the 2-ΔΔCT method.

Example 9

C34 and analogs protect against NEC induced intestinal injury.

NEC model C57/BL6 7-8 day old mice, subjected to NEC model with compounds mixed in NEC formula 10 mg/kg (2 mg/kg/feed or 10 mg/kg/day divided in 5 feeds). Control (Breast-fed) and NEC mice were sacrificed at same time on day 5 of treatments, small intestine (terminal ileum) was fixed in 4% paraformaldehyde, processed for paraffin blocks, sectioned in 5 μm slices and stained with hematoxylin and eosin staining and imaged using EVOS imaging system.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound having the following formula:

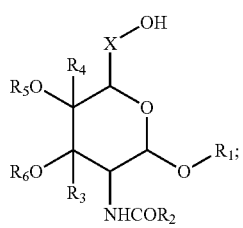

(I)

wherein $R_1$ is a $C_3$-$C_6$ branched or cyclic alkane, $R_2$ is H, or $C_1$-$C_4$ alkyl, $R_3$, $R_4$, $R_5$ and $R_6$ are each individually $C_2$-$C_6$ alkyl, X is $C_1$-$C_3$ alkyl, or a salt, solvate or stereoisomer thereof.

2. A compound having the formula:

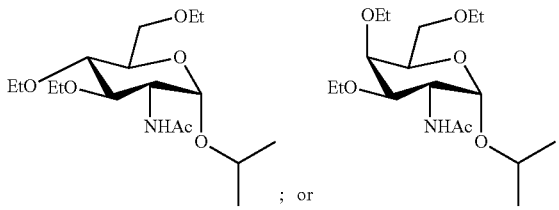

or a salt, solvate or stereoisomer thereof.

3. A pharmaceutical composition comprising a therapeutically effective amount of a compound of claim 1 and a pharmaceutically acceptable carrier.

4. A pharmaceutical composition comprising a therapeutically effective amount of a compound of claim 2 and a pharmaceutically acceptable carrier.

5. The pharmaceutical composition of claim 3, further comprising an effective amount of at least one additional biologically active agent.

6. The pharmaceutical composition of claim 5, wherein the least one additional biologically active agent is an anti-inflammatory agent.

7. A method for treating an infectious disorder, an inflammatory disorder, or a traumatic injury in a subject in need thereof comprising administering to the subject an effective amount of a compound of claim 1 or a pharmaceutical composition thereof.

8. The method of claim 7, wherein the inflammatory disorder comprises an intestinal inflammatory disorder.

9. The method of claim 7, wherein the inflammatory disorder comprises a cardiovascular inflammatory disorder.

10. The method of claim 7, wherein the inflammatory disorder comprises a pulmonary inflammatory.

11. A method for treating an infectious disorder, an inflammatory disorder, or a traumatic injury in a subject in need thereof comprising administering to the subject an effective amount of a compound of claim 6 or a pharmaceutical composition thereof.

12. The pharmaceutical composition of claim 4, further comprising an effective amount of at least one additional biologically active agent.

13. The pharmaceutical composition of claim 12, wherein the least one additional biologically active agent is an anti-inflammatory agent.

14. The method of claim 11, wherein the inflammatory disorder comprises an intestinal inflammatory disorder.

15. The method of claim 11, wherein the inflammatory disorder comprises a cardiovascular inflammatory disorder.

16. The method of claim 11, wherein the inflammatory disorder comprises a pulmonary inflammatory.

* * * * *